United States Patent
Pasquier et al.

(10) Patent No.: US 10,966,671 B2
(45) Date of Patent: Apr. 6, 2021

(54) METHODS AND APPARATUS TO CORRECT THE MEASUREMENT OF WATER EQUIVALENT DIAMETER IN COMPUTED TOMOGRAPHY WHEN PATIENTS ARE MISCENTERED

(71) Applicant: General Electric Company, Schenectady, NY (US)

(72) Inventors: Hugo Pasquier, Paris (FR); Sylvie Jacquot-Ingles, Buc (FR); Dominic Crotty, Waukesha, WI (US); Alain Luciani, Paris (FR); François Gardavaud, Paris (FR)

(73) Assignee: General Electric Company, Schenectady, NY (US)

( * ) Notice: Subject to any disclaimer, the term of this patent is extended or adjusted under 35 U.S.C. 154(b) by 297 days.

(21) Appl. No.: 16/013,317

(22) Filed: Jun. 20, 2018

(65) Prior Publication Data
US 2018/0360399 A1  Dec. 20, 2018

Related U.S. Application Data

(60) Provisional application No. 62/522,371, filed on Jun. 20, 2017.

(51) Int. Cl.
| | |
|---|---|
| *A61B 6/00* | (2006.01) |
| *A61B 6/03* | (2006.01) |
| *A61B 6/04* | (2006.01) |

(52) U.S. Cl.
CPC .............. *A61B 6/405* (2013.01); *A61B 6/032* (2013.01); *A61B 6/04* (2013.01); *A61B 6/488* (2013.01);
(Continued)

(58) Field of Classification Search
CPC .......... A61B 6/405; A61B 6/032; A61B 6/04; A61B 6/488; A61B 6/544; A61B 6/588; A61B 6/589
See application file for complete search history.

(56) References Cited

U.S. PATENT DOCUMENTS

| | | | | |
|---|---|---|---|---|
| 5,457,724 A | * | 10/1995 | Toth ....................... | A61B 6/032 378/205 |
| 6,628,744 B1 | * | 9/2003 | Luhta ..................... | A61B 6/032 378/15 |

(Continued)

OTHER PUBLICATIONS

Li et al., "Comparison of topogram-based body size indices for CT dose consideration and scan protocol optimization", Medical Physcis 39, 3456 (2012); doi: 10.1118/1.4718569, Published by the American Association of Physicists in Medicine, 11 pages.

*Primary Examiner* — Blake C Riddick

(57) ABSTRACT

Methods, apparatus, systems and articles of manufacture to correct the measurement of water equivalent diameter in Computed Tomography (CT) imaging when patients are miscentered are disclosed. A disclosed example apparatus includes a patient size characteristic calculator to calculate a set of patient size characteristics for a set of axial slices along a height of the patient. The apparatus further includes a patient size characteristic corrector module to calculate a set of correction factors for the set of patient size characteristics and apply the set of correction factors to the set of patient size characteristics. The apparatus further includes a computation manager to utilize a set of corrected patient size characteristics for the set of axial slices along the height of the patient to perform a CT scan on the patient by modulating an X-ray current to control a radiation dose applied to the patient.

21 Claims, 11 Drawing Sheets

(52) U.S. Cl.
CPC .............. *A61B 6/544* (2013.01); *A61B 6/588* (2013.01); *A61B 6/589* (2013.01)

(56) References Cited

U.S. PATENT DOCUMENTS

| | | | | |
|---|---|---|---|---|
| 2002/0114503 | A1* | 8/2002 | Klotz | G06T 7/0012 |
| | | | | 382/131 |
| 2003/0054419 | A1* | 3/2003 | Slawin | G01N 33/57434 |
| | | | | 435/7.23 |
| 2003/0185343 | A1* | 10/2003 | Horiuchi | G01N 23/046 |
| | | | | 378/108 |
| 2004/0208277 | A1* | 10/2004 | Morikawa | A61B 6/032 |
| | | | | 378/4 |
| 2005/0089135 | A1* | 4/2005 | Toth | A61B 6/032 |
| | | | | 378/16 |
| 2005/0089138 | A1* | 4/2005 | Toth | A61B 6/469 |
| | | | | 378/20 |
| 2008/0296505 | A1* | 12/2008 | Cooke | G01T 1/2985 |
| | | | | 250/363.04 |
| 2010/0239146 | A1* | 9/2010 | Suzuki | G06T 11/005 |
| | | | | 382/131 |
| 2013/0114799 | A1* | 5/2013 | Yamakawa | A61B 6/14 |
| | | | | 378/207 |
| 2017/0318652 | A1* | 11/2017 | Meiler | A61B 6/582 |
| 2018/0174335 | A1* | 6/2018 | Yamakawa | A61B 6/5258 |

\* cited by examiner

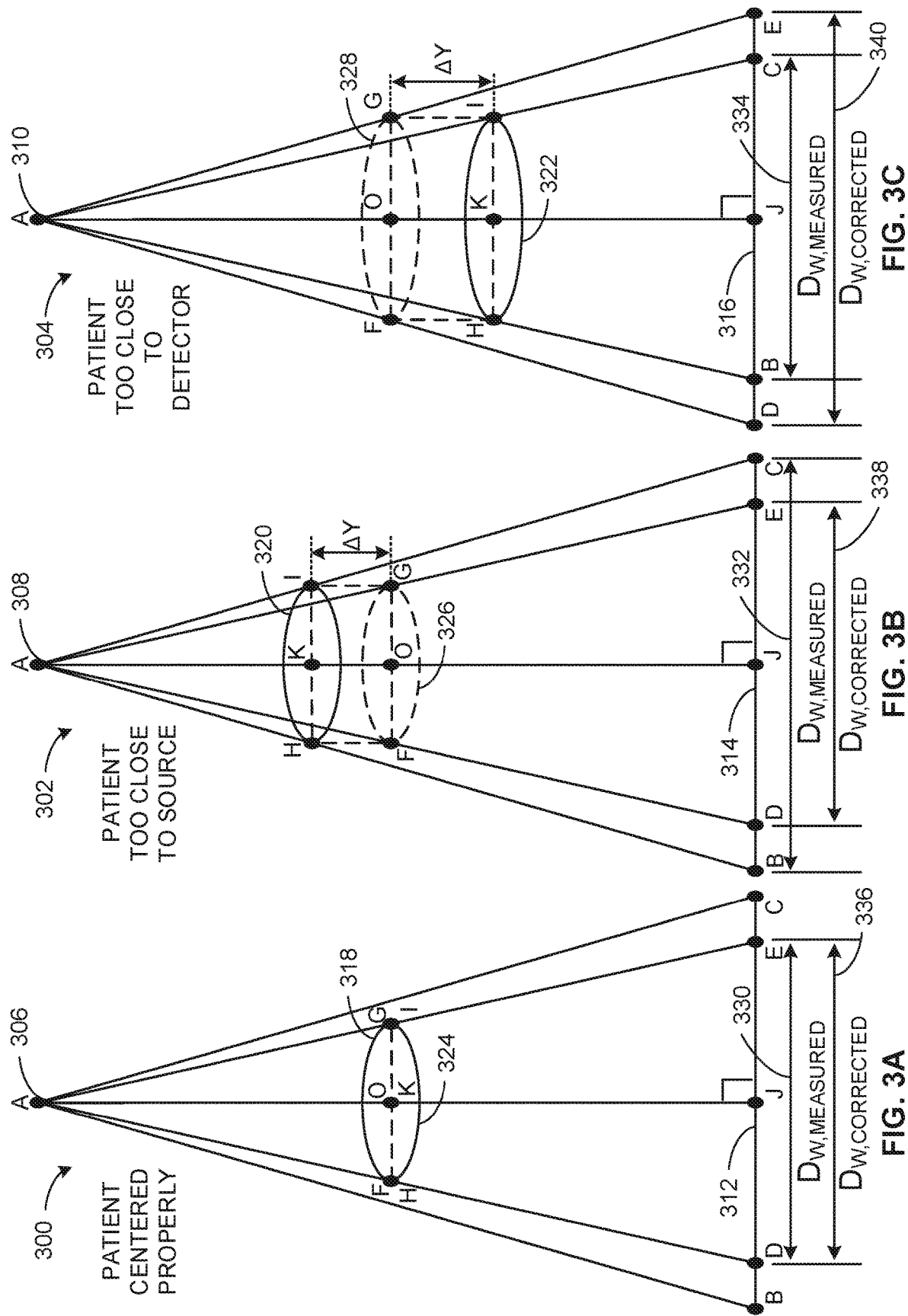

METHODS AND APPARATUS TO CORRECT THE MEASUREMENT OF WATER EQUIVALENT DIAMETER IN COMPUTED TOMOGRAPHY WHEN PATIENTS ARE MISCENTERED

RELATED APPLICATION

This patent claims priority to U.S. Provisional Patent Application Ser. No. 62/522,371 filed Jun. 20, 2017, entitled "METHODS AND APPARATUS TO CORRECT THE MEASUREMENT OF WATER EQUIVALENT DIAMETER IN COMPUTER TOMOGRAPHY WHEN PATIENTS ARE MISCENTERED." The entirety of U.S. Patent Application Ser. No. 62/522,371 is incorporated herein by reference.

FIELD OF THE DISCLOSURE

This disclosure relates generally to Computed Tomography (CT) imaging, and, more particularly, to methods and apparatus to correct the measurement of water equivalent diameter in Computed Tomography imaging when patients are miscentered.

BACKGROUND

In recent years, usage rates of Computed Tomography (CT) scans have been on the rise. Traditionally, CT scans generally apply a significant dose of radiation to the example patient undergoing the scan. Further, the dose of radiation applied to the example patient is determined by a measured size of the example patient. In general, if the example patient size is overestimated, a larger than required dose of radiation will be applied to the example patient. Conversely, if the example patient size is underestimated, a smaller than required dose of radiation will be applied to the example patient, and the imaging quality of the scan will consequently be reduced.

In the pursuit of optimizing the dose of radiation applied to a patient, gains can be made by acquiring an accurate measure of patient size prior to completing the scan increasing the accuracy of patient size will, on average, decrease the dose of radiation applied to the example patient while simultaneously increasing the quality of the CT scan output image.

BRIEF DESCRIPTION OF THE DRAWINGS

FIG. 3A-3C illustrate an example water equivalent diameter measurement for an example patient in an example CT scanner of FIG. 1, wherein the example patient is centered at a different location in the example CT scanner in each of FIGS. 3A, 3B, and 3C.

The figures are not to scale. Instead, to clarify multiple layers and regions, the thickness of the layers can be enlarged in the drawings. Wherever possible, the same reference numbers will be used throughout the drawing(s) and accompanying written description to refer to the same or like parts.

BRIEF SUMMARY

Figure 1:
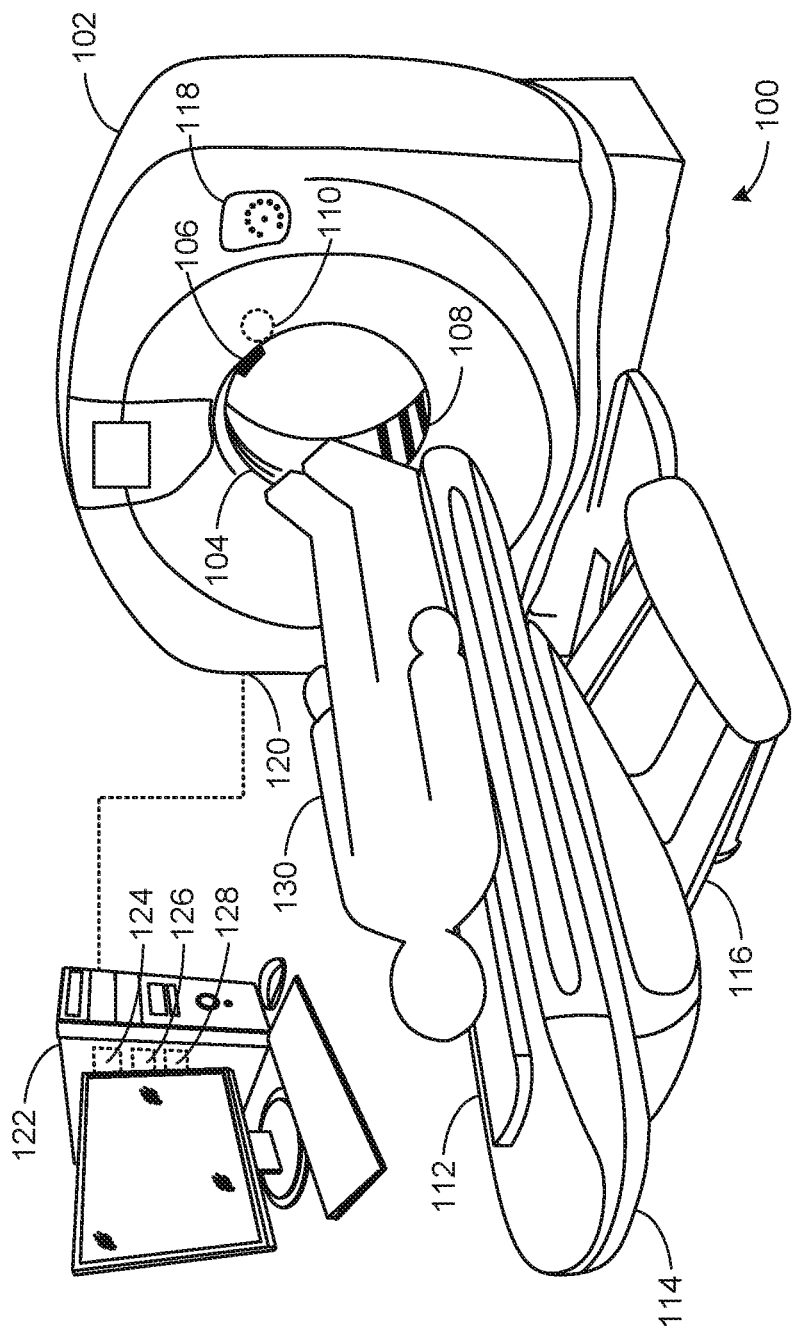
FIG. 1 is an illustrated example Computed Tomography (CT) scanner and computation manager in which the examples disclosed herein can be implemented.

Methods, apparatus, and articles of manufacture to correct the measurement of water equivalent diameter in Computed Tomography when patients are miscentered are disclosed.

Certain examples provide an example apparatus to correct a patient size characteristic in Computed Tomography (CT) when a patient is miscentered. The apparatus includes a patient size characteristic calculator to calculate a set of patient size characteristics for a set of axial slices along a height of the patient. The apparatus further includes a patient size characteristic corrector module to calculate a set of correction factors for the set of patient size characteristics based on a set of patient miscentering distances for the set of axial slices along the height of the patient and apply the set of correction factors to the set of patient size characteristics for the set of axial slices along the height of the patient. The apparatus further includes a computation manager to utilize a set of corrected patient size characteristics for the set of axial slices along the height of the patient to perform a CT scan on the patient by modulating an X-ray current to control a radiation dose applied to the patient.

Certain examples provide an example method for correcting patient size characteristics in Computed Tomography (CT) when patients are miscentered. The method includes calculating, using a processor, a set of patient size characteristics for a set of axial slices along a height of the patient. The method further includes calculating, using the processor, a set of correction factors for the set of patient size characteristics based on a set of patient miscentering distances for the set of axial slices along the height of the patient. The method further includes applying, using the processor, the set of correction factors to the set of patient size characteristics for the set of axial slices along the height of the patient. The method further includes utilizing, using the processor, a set of corrected patient size characteristics for the set of axial slices along the height of the patient to perform a CT scan on the patient by modulating an X-ray current to control a radiation dose applied to the patient.

Certain examples provide an example non-transitory computer readable storage medium comprising machine-readable instructions that, when executed by a processor, cause a machine to at least calculate a set of patient size characteristics for a set of axial slices along a height of a patient, calculate a set of correction factors for the set of patient size characteristics based on a set of patient miscentering distances for the set of axial slices along the height of the patient, apply the set of correction factors to the set of patient size characteristics for the set of axial slices along the height of the patient, and utilize a set of corrected patient size characteristics for the set of axial slices along the height of the patient to perform a CT scan on the patient by modulating an X-ray current to control a radiation dose applied to the patient.

DETAILED DESCRIPTION

In the field of Computed Tomography (CT) scanning, measuring the size of a patient prior to completing the scan is done for two reasons: first, to precisely calculate the dose of radiation to be administered to the example patient and secondly, to optimize one or more scan parameter(s) to a patient's body. In general, underestimating the size of the example patient will result in sub-optimal image quality which could necessitate a second scan to be completed on the example patient. Conversely, overestimating the size of the example patient will result in the example patient receiving a larger than necessary dose of radiation. With usage rates of CT scans on the rise, minimizing or otherwise reducing the dose of radiation a patient receives as well as minimizing or otherwise reducing the number of scans involved is important.

One method of measuring a patient prior to scanning is using an initial topographic scan, called a localizer (or a "scout"), on the example patient. This scout gives a rudimentary image of the example patient which can then be used to calculate a width of a patient (B), and a thickness of a patient (A) at one or more axial cross sections. In some such examples, the shape of the patient will be further estimated as an ellipse with a major diameter B, and a minor diameter A, the area of which is as calculated below:

$$\text{Area} = \frac{\pi}{4} AB \qquad \text{Equation (1)}$$

Further from minor diameter A, major diameter B, and ellipse area as calculated above in Equation (1), Projection Measure (PM), Projection Area (PA), and Oval Ratio (OR) can be calculated. PM, as used herein, is a measure of the X-ray attenuation at the thickest point of the patient. PA, as used herein, is a measure of the total X-ray attenuation of the patient. OR, as used herein, is a ratio of the major diameter and minor diameter of the patient when the patient is estimated as an ellipse. Introducing the variable μ, further defined as an X-ray attenuation coefficient of the patient, definitions for each of PM, PA, and OR, respectively, are as follows:

$$PM = \mu A \qquad \text{Equation (2)}$$

$$PA = \mu * \text{Area} \qquad \text{Equation (3)}$$

$$OR = \frac{B}{A} \qquad \text{Equation (4)}$$

Further, Water Equivalent Diameter ($D_w$), an industry gold standard for size metrics, of the example patient can be calculated from PA, thereby calculating Water Equivalent Diameter from characteristics of an initial topographic scan. The equation to determine Water Equivalent diameter is as follows:

$$D_w = PA * \text{const.} \qquad \text{Equation (5)}$$

One issue related to this approach involves the centering of the example patient in the view of the X-ray tube. When miscentered, a patient's size will be distorted due to the conical shape of the beam emitted from the X-ray emitter. When miscentered towards the emitter, the example patient's size can be overestimated. Conversely, the example patient's size can be underestimated when miscentered towards the detector. Currently, solutions to this problem are quite limited.

A new solution, put forth by the methods, apparatus, and articles of manufacture disclosed herein, applies a correction factor to $D_w$ based upon a determined miscentering distance. Miscentering distance can be determined using a lateral (e.g., taken from the side of an example patient) localizer and is measured for each axial slice along the height of the example patient. After calculating $D_{w,measured}$ (a measured $D_w$ value) for each slice of the example patient from an anteroposterior (e.g., taken from the top of an example patient) scout or posteroanterior (e.g., taken from the bottom of an example patient) scout, the correction factor is applied to calculate a corrected $D_w$ value, $D_{w,corrected}$. The aforementioned correction factor, which uses the miscentering distance found previously in conjunction with a property of similar triangles, can accurately determine a value for $D_w$ without regard to an amount and/or direction of patient miscentering. With that in mind, use of the described correction factor can increase the accuracy of radiation dose administered to the example patient, helping to ensure that higher quality CT images are acquired at more optimal radiation doses.

Turning to the figures, FIG. 1 is an illustration of an example system 100 in which example systems and methods disclosed herein can be implemented. The example system 100 includes an example CT scanner 102 which can, in some examples, further include an X-ray tube 104 which can, in some examples, further include an X-ray emitter 106, one or more X-ray detector(s) 108, and a rotational actuator 110, a patient bed 112 which can, in some examples, contain an axial actuator 114, and a vertical actuator 116, an input panel 118, and a data port 120. The example system 100 further includes a computation manager 122, described in further detail below in conjunction with FIG. 6, and can, in some examples, include a patient size characteristic calculator 124, a patient size characteristic corrector module 126, and a processor 128. Further, while not a part of the example system 100, FIG. 1 shows an illustrated example patient 130 in relation to the patient bed 112, X-ray emitter 106, and X-ray detector(s) 108.

In the illustrated example of FIG. 1, the CT scanner 102 includes hardware (e.g., sensors, actuators, inputs, outputs, etc.) to complete a full CT scan on the example patient 130. In some such examples, the CT scanner 102 includes the example X-ray tube 104, the example patient bed 112, the example input panel 118, and the example data port 120.

Additionally, the X-ray tube 104 rotates about the center of the example patient bed 112 and the example patient 130 and further includes the X-ray emitter 106, one or more X-ray detector(s) 108, and the rotational actuator 110. In some such examples, the X-ray emitter 106 emits a controlled X-ray signal, in an approximate cone shape, from an approximate point source located at a predetermined position in the X-ray tube 104.

The controlled X-ray signal emitted by the X-ray emitter 106 travels through at least one of the example patient bed 112 and the example patient 130 which further attenuate the X-ray signal based on various criteria (e.g., size of the example patient bed 112 and the example patient 130, material properties of the example patient bed 112 and the example patient 130, etc.). Further, the one or more X-ray detector(s) 108, distributed evenly over the region of the X-ray tube 104 at which the X-ray signal emitted by the X-ray emitter 106 is directed, receive(s) the X-ray signal attenuated by the example patient bed 112 and the example patient 130.

Further, the X-ray tube 104 includes the rotational actuator 110. The rotational actuator 110 rotates the X-ray tube 104, in examples where the example patient 130 is properly centered, about a centerline of the example patient 130. Further, in rotating the X-ray tube 104, the rotational actuator 110 rotates the X-ray emitter 106 and the one or more X-ray detector(s) 108 at a similar rotational velocity. This helps ensure that the one or more X-ray detector(s) 108 remain located within the region of the X-ray tube 104 at which the example X-ray signal emitted by the X-ray emitter 106 is directed.

Additionally, CT scanner 102 includes the example patient bed 112, on which the example patient 130 lies horizontal upon during an example CT scan. Further, the example patient bed 112 includes the axial actuator 114 and vertical actuator 116. The axial actuator 114 can, in some such examples, translate the example patient bed 112, and thereby the example patient 130, along a line perpendicular to an opening of the X-ray tube 104. Further, the vertical actuator 116 translates the example patient bed 112, and thereby the example patient 130, along a line perpendicular to a surface upon which the CT scanner 102 is placed. In some such examples, the vertical actuator 116 translates a patient bed 112, and thereby an example patient 130, to an approximate isocenter of an opening of the X-ray tube 104.

Additionally, the input panel 118 can allow a user (e.g., a technician, a radiologist, a doctor, a nurse, an individual with skill in conducting CT scans, etc.) to at least one of control a CT scan and modify parameters of a CT scan. In some such examples, the input panel 118 can allow the user to initiate a CT scan. In other such examples, the input panel 118 can allow the user to move the example patient 130 to an approximate isocenter of an opening of the X-ray tube 104. In other such examples, the input panel 118 can allow the user to at least one of pause and abort an in progress CT scan. In other such examples, the input panel 118 can allow the user to verify CT parameters as determined by the CT scanner 102. In other such examples, the input panel 118 can allow the user to abort the CT scan at any point during the scan. Note that the above examples are not meant to be limiting, and that any combination and/or permutation of commands entered with the input panel 118 by the user are covered within this scope of this patent.

In some such examples, the input panel 118 can be implemented by, for example, an audio sensor, a microphone, a camera (still or video), a keyboard, a button, a mouse, a touchscreen, a track-pad, a trackball, isopoint and/or a voice recognition system.

In some such examples, CT scanner 102 further includes the data port 120. The data port 120 can at least one of transfer data to and receive data from the example computation manager 122. The data port 120 can further at least one of transfer data to and receive data from any component of the CT scanner 102, which can include the X-ray tube 104, the X-ray emitter 106, the one or more X-ray detector(s) 108, the rotational actuator 110, the example patient bed 112, the axial actuator 114, the vertical actuator 116, and the input panel 118. In some such examples, the data port 120 can be implemented by any type of interface standards, such as an Ethernet interface, a universal serial bus (USB), and/or a PCI express interface.

Figure 2A:
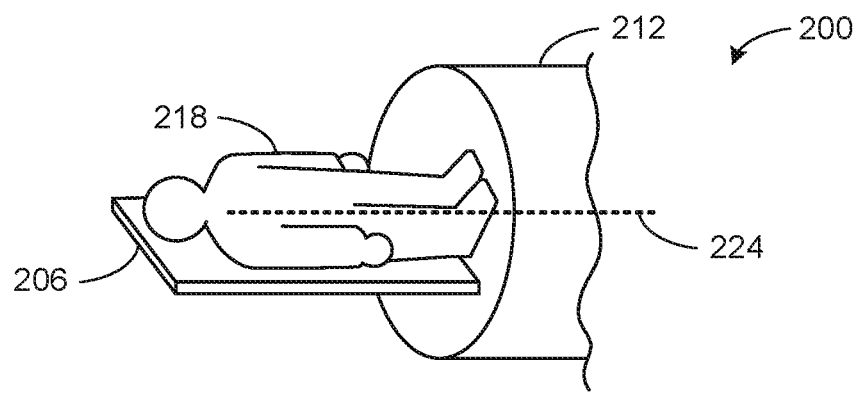
FIG. 2A-2C illustrate an example patient in the example CT scanner of FIG. 1, wherein the example patient is centered at a different location in the example CT scanner in each of FIGS. 2A, 2B, and 2C.
Figure 2B:
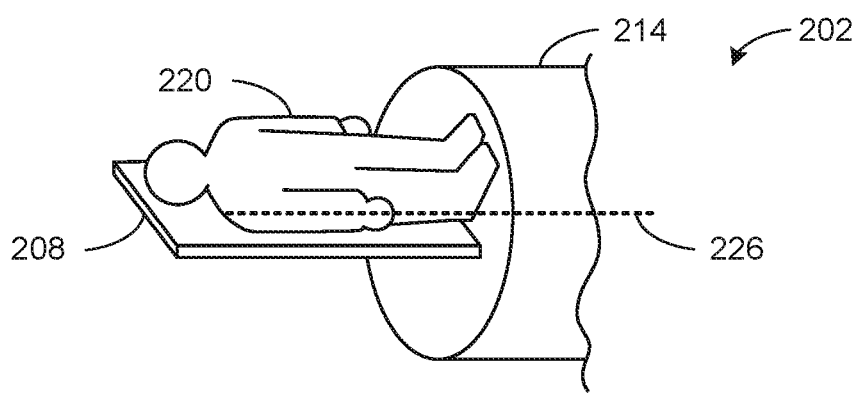
Figure 2C:
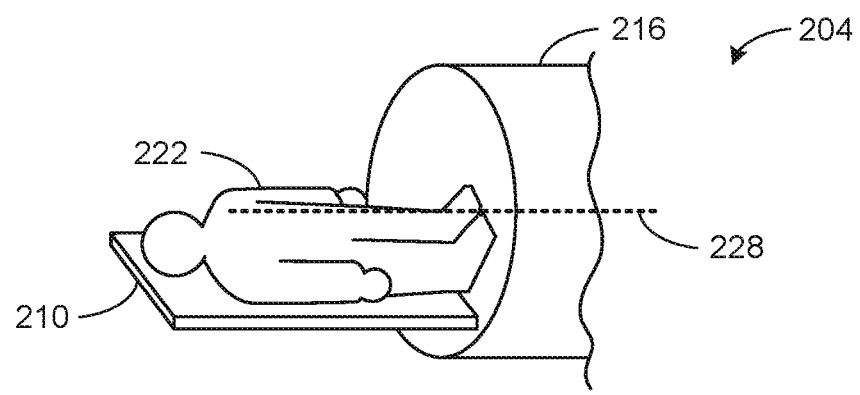

FIG. 2A-2C illustrate three (3) patient bed centering locations 200, 202, and 204 and include three (3) example patient beds 206, 208, and 210, three (3) example X-ray tubes 212, 214, and 216, three (3) example patients 218, 220, and 222, and three (3) example X-ray tube centerlines 224, 226, and 228.

In the illustrated example of FIG. 2A, further illustrating the example patient bed centering location 200, the example patient bed 206 is positioned in the example X-ray tube 212 such that the example patient 218 is properly centered at the example X-ray tube centerline 224. In such an example, described in further detail below, a correction factor is not required to accurately estimate a set of patient size characteristics for the example patient 218.

Additionally or alternatively, in the illustrated example of FIG. 2B, further illustrating the example patient bed centering location 202, the example patient bed 208 is positioned in the example X-ray tube 214 such that the example patient 220 is centered above the example X-ray tube centerline 224. In such an example, described in further detail below, a set of patient size characteristics would be overestimated without the use of a correction factor and the example patient 220 undergoing a CT scan would receive a larger than necessary dose of radiation.

Additionally or alternatively, in the illustrated example of FIG. 2C, further illustrating the example patient bed centering location 204, the example patient bed 210 is positioned in the example X-ray tube 216 in such a manner that the example patient 222 is centered below the example X-ray tube centerline 228. In such an example, described in further detail below, a set of patient size characteristics would be underestimated without the use of a correction factor and the example patient 222 undergoing a CT scan would receive a smaller than necessary dose of radiation, potentially reducing the imaging quality of the scan.

FIG. 3A-3C illustrate a cross sectional view of the three (3) patient bed centering locations 200, 202, and 204 of FIG. 2A-2C, and include example patient centering locations 300, 302, and 304, example X-ray emitter locations 306, 308, and 310 (further denoted by A), example X-ray detector locations 312, 314, and 316 (further denoted by J), example actual patient cross sections 318, 320, and 322 (further denoted by HKI), example centered patient cross sections 324, 326, and 328 (further denoted by FOG), example measured water equivalent diameters 330, 332, and 334 (further denoted by at least one of BC or DE), and example corrected water equivalent diameters 336, 338, and 340 (further denoted by DE).

In the illustrated example of FIG. 3A, patient centering location 300 at which the example patient is centered equidistant from the example X-ray emitter location 306, and the example X-ray detector location 312 is further illustrated (e.g., line AK and line KJ are equal in length). In such an example, the example actual patient cross section 318 (e.g., HKI) is located at a same position as the example centered patient cross section 324 (e.g., FOG). Further in such an example, a patient miscentering distance is equal to zero (0) and a water equivalent diameter correction factor is equal to one (1). As a result, the example measured water equivalent diameter 330 (e.g., DE) is equal to the corrected water equivalent diameter 336 (e.g., DE).

In the illustrated example of FIG. 3B, patient centering location 302 at which the example patient is centered closer to the example X-ray emitter location 308 than the example X-ray detector location 314 is further illustrated (e.g., line AK is shorter than line KJ). In such an example, the example actual patient cross section 320 (e.g., HKI) is located closer to the example X-ray emitter location 308 than the example centered patient cross section 326 (e.g., FOG). Further in such an example, a patient miscentering distance is greater than zero (0) and a water equivalent diameter correction value is less than one (1). As a result, the example measured water equivalent diameter 332 (e.g., BC) is greater than the corrected water equivalent diameter 338 (e.g., DE).

In the illustrated example of FIG. 3C, patient centering location 304 at which the example patient is centered farther from the example X-ray emitter location 310 than the example X-ray detector location 316 is further illustrated (e.g., line AK is longer than line KJ). In such an example, the example actual patient cross section 322 (e.g., HKI) is located farther from the example X-ray emitter location 310 than the example centered patient cross section 328 (e.g., FOG). Further in such an example, a patient miscentering distance is less than zero (0) and a water equivalent diameter correction value is greater than one (1). As a result, the example measured water equivalent diameter 334 (e.g., BC) is less than the corrected water equivalent diameter 340 (e.g., DE).

Figure 4:
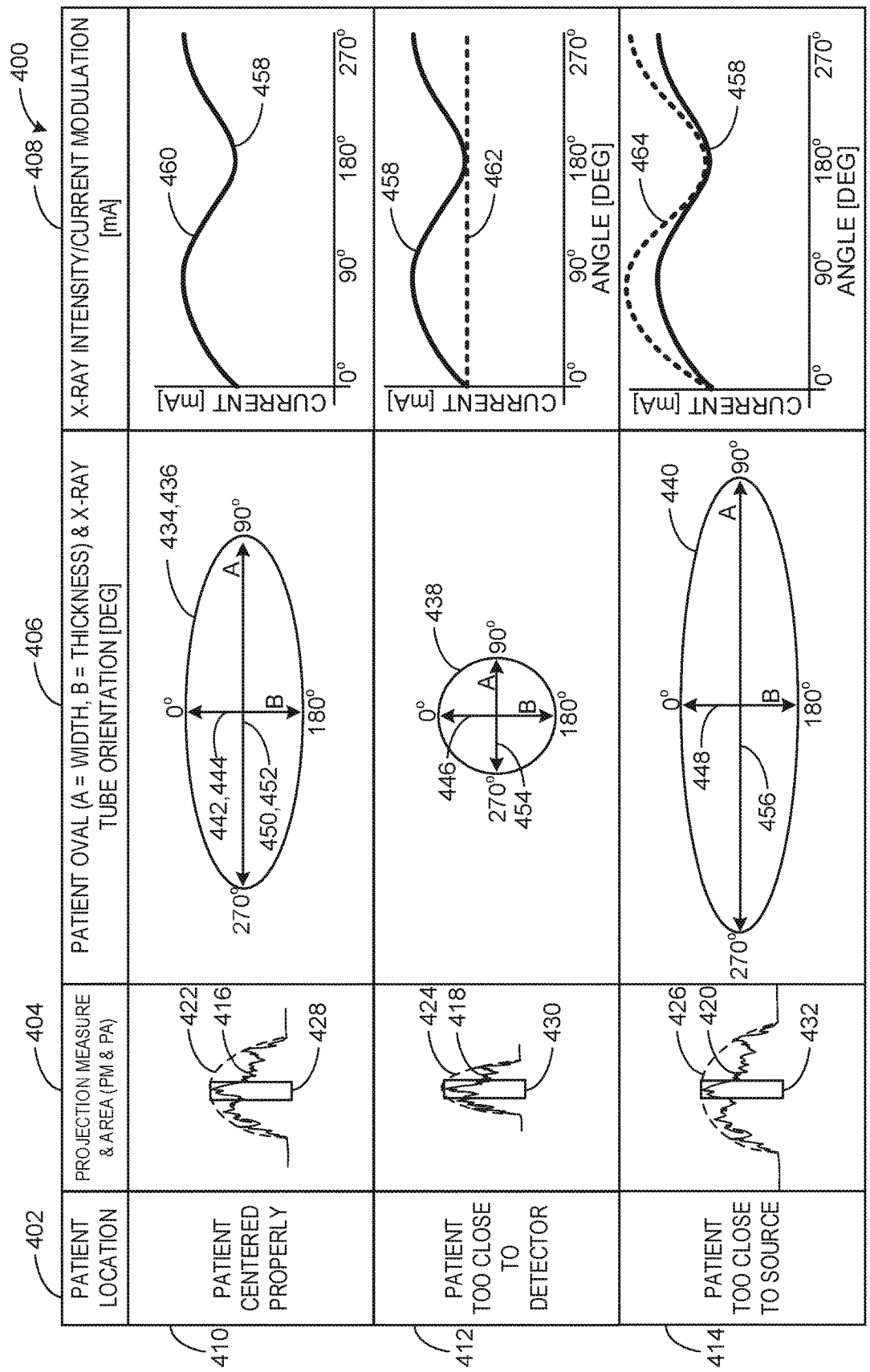
FIG. 4 illustrates an example patient oval shape and an example graph of X-ray intensity modulation for an example patient, wherein the example patient is centered at various locations in the example CT scanner of FIG. 1.

FIG. 4 illustrates an example table 400 displaying characteristics further including, in some such examples, example patient location output 402, example projection measure and area 404, example measured patient oval shape output 406, and example X-ray intensity/current modulation plots 408 for one or more example row(s) 410, 412, and/or 414. Further, the example table 400 includes example X-ray attenuation plot(s) 416, 418, and/or 420, example Projection Area(s) 422, 424, and/or 426, and example Projection Measure(s) 428, 430, and/or 432. Further included in the example table 400 are an example actual patient oval 434, example measured patient oval(s) 436, 438, and/or 440, an example actual patient thickness 442, example measured patient thickness(es) 444, 446, and/or 448, an example actual patient width 450, example measured patient width(s) 452, 454, and/or 456, an example desired X-ray intensity/current modulation waveform 458, and example output X-ray intensity/current modulation waveform(s) 460, 462, and/or 464. Further, the example desired X-ray intensity/current modulation waveform 458 and example output X-ray intensity/current modulation waveform(s) 460, 462, and/or 464 are described for one (1) complete rotation (e.g., from 0 degrees to 360 degrees, wherein 0 degrees and 360 degrees are defined as above the example patient, 90 degrees is defined as to the right of the example patient, 180 degrees is defined as below the example patient, and 270 degrees is defined as to the left of the example patient) about an example patient.

Further detailing row 410 of the example table 400 of FIG. 4, the example patient location output 402 in such an example is "patient centered properly". In such an example, each of the example X-ray attenuation plot 416, example Projection Area 422, and example Projection Measure 428 accurately measure a size of an example patient. Further in such an example, the example measured patient oval 436 is further defined by the example measured patient thickness 444, and the example measured patient width 452. Further, each of the example measured patient oval 436, example measured patient thickness 444, and example measured patient width 452 match the example actual patient oval 434, the example actual patient thickness 442, and the example actual patient width 450, respectively. In response to the example actual patient oval 434 matching the measured patient oval 436, the output X-ray intensity/current modulation waveform 460 for such an example matches the desired X-ray intensity/current modulation waveform 458.

Further detailing row 412 of the example table 400 of FIG. 4, the example patient location output 402 in such an example is "patient too close to the detector". In such an example, each of the example X-ray attenuation plot 418, and example Projection Area 424 underestimate a size of an example patient while the example Projection Measure 430 accurately measures a size of an example patient. Further in such an example, the example measured patient oval 438 is further defined by the example measured patient thickness 446, and the example measured patient width 454. Further, the example measured patient thickness 446 matches the example actual patient thickness 442. Conversely, the example measured patient oval 438, and the example measured patient width 452 are smaller than the example actual patient oval 434, and the example actual patient width 450, respectively. In response to the example measured patient oval 438, and the example measured patient width 454 being smaller than the example actual patient oval 434, and the example actual patient width 450, respectively, the output X-ray intensity/current modulation waveform 462 for such an example is smaller than the desired X-ray intensity/current modulation waveform 458. This can result in imaging quality of the scan being reduced at orientations at which the output X-ray intensity/current modulation waveform 462 is less than the desired X-ray intensity/current modulation waveform 458.

Further detailing row 414 of the example table 400 of FIG. 4, the example patient location output 402 in such an example is "patient too close to the source". In such an example, each of the example X-ray attenuation plot 420, and example Projection Area 426 overestimate a size of an example patient while the example Projection Measure 430 accurately measures a size of an example patient. Further in such an example, the example measured patient oval 440 is further defined by the example measured patient thickness 448, and the example measured patient width 456. Further, the example measured patient thickness 448 matches the example actual patient thickness 442. Conversely, the example measured patient oval 438, and the example measured patient width 452 are larger than the example actual patient oval 434, and the example actual patient width 450, respectively. In response to the example measured patient oval 440, and the example measured patient width 456 being larger than the example actual patient oval 434, and the example actual patient width 450, respectively, the output X-ray intensity/current modulation waveform 464 for such an example is larger than the desired X-ray intensity/current modulation waveform 458. This can result in an unnecessarily large radiation dose to be applied to a patient at orientations at which the output X-ray intensity/current modulation waveform 464 is greater than the desired X-ray intensity/current modulation waveform 458.

Figure 5:
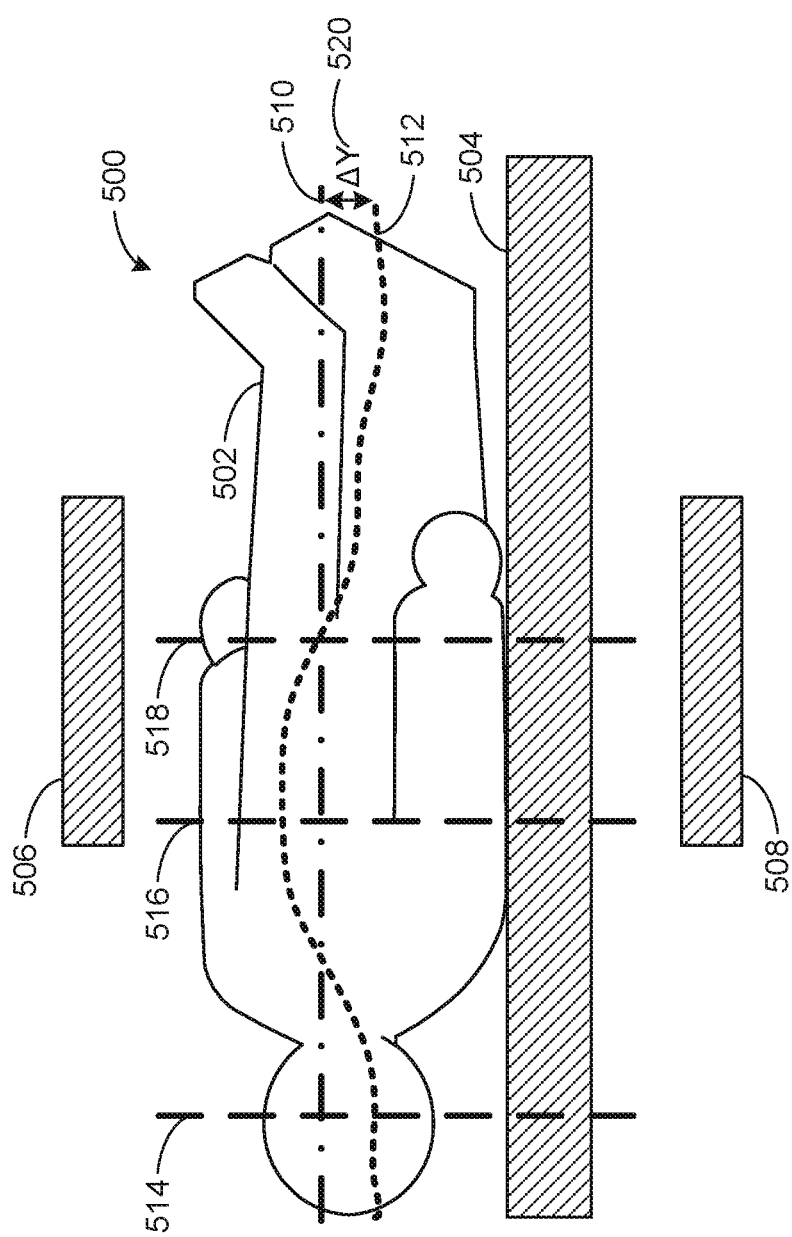
FIG. 5 illustrates an example patient centering location across a height of an example patient in an example CT scanner of FIG. 1.

FIG. 5 is an illustrated cross sectional view in the lateral orientation of an example patient 502, laying horizontal to an example patient bed 504, which is approximately centered between an Example X-ray emitter 506, and an example X-ray detector 508. The illustrated cross sectional view of FIG. 5 further includes an example CT scanner centerline 510, an example patient centerline 512, one or more axial slice(s) 514, 516, and/or 518 and an example patient miscentering distance 520 (further denoted by $\Delta Y$)

In the illustrated example of FIG. 5, the example patient miscentering distance 520 can further be defined by the distance between the example CT scanner centerline 510 and the example patient centerline 512 for a subset of patient axial slices, in some such examples axial slice(s) 514, 516, and/or 518, along a height of the example patient 502.

Further, for the example axial slice 514, an example distance between the example X-ray emitter 506 and the example CT scanner centerline 510 is smaller than an example distance between the example X-ray emitter 506 and the example patient centerline 512. Therefore, at axial slice 514, the example patient 502 is too close to the example X-ray detector 508.

For the example axial slice 516, an example distance between the example X-ray emitter 506 and the example CT scanner centerline 510 is larger than an example distance between the example X-ray emitter 506 and the example patient centerline 512. Therefore, at axial slice 516, the example patient 502 is too close to the example X-ray emitter 506.

For the example axial slice 518, an example distance between the example X-ray emitter 506 and the example CT scanner centerline 510 is equal to an example distance between the example X-ray emitter 506 and the example patient centerline 512. Therefore, at axial slice 518, the example patient 502 is properly centered between the example X-ray emitter 506 and the example X-ray detector 508.

Figure 6:
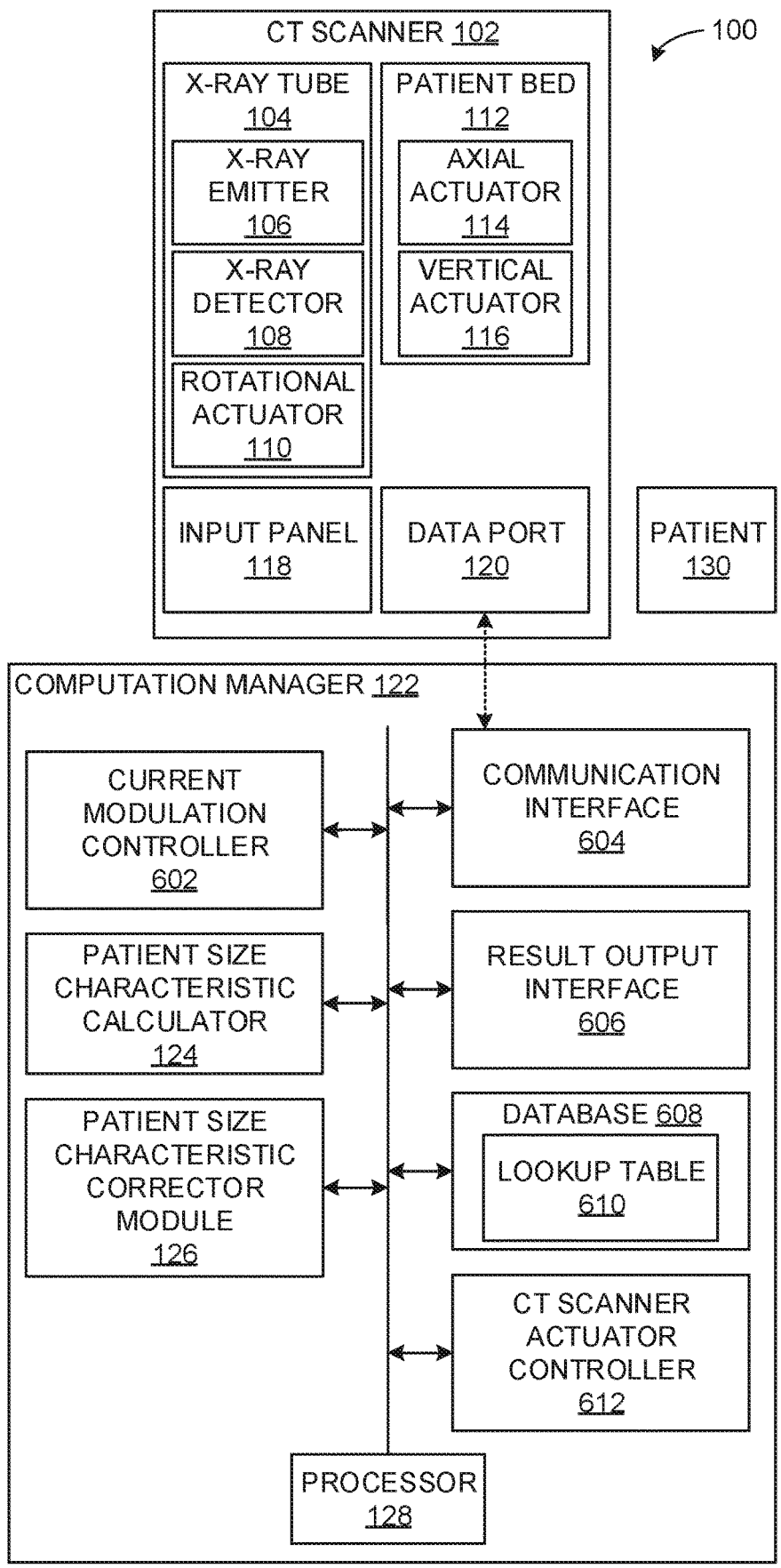
FIG. 6 is a block diagram of the example Computed Tomography (CT) Scanner and computation manager in which the examples disclosed herein can be implemented.

Turning to FIG. 6, a block diagram further detailing the example system 100 in which the examples disclosed herein can be implemented is provided. The example system 100 includes the example CT scanner 102, which was further described in conjunction with FIG. 1 and can, in some examples, include the example X-ray tube 104 which can, in some examples include the example X-ray emitter 106, the example one or more X-ray detector(s) 108, and the example rotational actuator 110, the example patient bed 112 which can, in some examples, include the example axial actuator 114, and the example vertical actuator 116, the example input panel 118, and the example data port 120. The example system 100 further includes the example computation manager 122 which can, in some examples, include the example patient size characteristic calculator 124, the example patient size characteristic corrector module 126, the example processor 128, an example current modulation controller 602, an example communication interface 604, an example result output interface 606, an example database 608 which can, in some examples, include an example lookup table 610, and an example CT scanner actuator controller 612. Further, while not a part of the example system 100, FIG. 6 includes the example patient 130.

In the illustrated example of FIG. 6, the computation manager 122 includes components to process inputs and outputs of the CT scanner 102. Further, the computation manager 122 includes the example patient size characteristic calculator 124, the example patient size characteristic corrector module 126, the processor 128, the current modulation controller 602, the communication interface 604, the result output interface 606, the database 608 which can, in some such examples, include the lookup table 610, and the CT scanner actuator controller 612.

The example patient size characteristic calculator 124 is further included in the computation manager 122. Generally, the example patient size characteristic calculator 124 calculates one or more patient size characteristic(s) based upon an example second CT scan localizer image, taken in at least one of an anteroposterior or posteroanterior orientation. In some such examples, the example patient size characteristic calculator 124 can calculate the water equivalent diameter of the example patient 130. Additionally or alternatively, the example patient size characteristic calculator 124 can calculate a thickness of the example patient 130. Additionally or alternatively, the example patient size characteristic calculator 124 can calculate a width of the example patient 130. Additionally or alternatively, the example patient size characteristic calculator 124 can calculate an oval ratio of the example the example patient 130. Additionally or alternatively, the example patient size characteristic calculator 124 can calculate any combination and/or permutation of patient size characteristic(s) set forth above. In some such examples, the example patient size characteristic calculator 124 can further apply one or more correction factor(s) as calculated by the example patient size characteristic corrector module 126 to one or more patient size characteristic(s) (e.g., the one or more patient size characteristic(s) is(are) multiplied by the one or more correction factor(s)) previously calculated by the example patient size characteristic calculator 124.

In the illustrated example of FIG. 6, the computation manager 122 further includes the example patient size characteristic corrector module 126, described in further detail below, which calculates one or more correction factor(s) for one or more patient size characteristic(s) calculated by the example patient size characteristic calculator 124.

Further, the computation manager 122 includes the processor 128. The processor 128 can, in some such examples, execute the processes set forth by at least one of the example patient size characteristic calculator 124, the example patient size characteristic corrector module 126, the current modulation controller 602, the communication interface 604, the result output interface 606, the database 608 which can, in some such examples, include the lookup table 610, and the CT scanner actuator controller 612. Further, the processor 128 of the example system 100 is hardware and can be implemented by one or more integrated circuits, logic circuits, microprocessors, or controllers from any desired family or manufacturer.

In the illustrated example of FIG. 6, the computation manager 122 further includes the current modulation controller 602. The current modulation controller 602 can control a current applied to the example X-ray emitter 106, thereby controlling a radiation dose applied to the example patient 130. In some such examples, the current modulation controller 602 can calculate a radiation dose to be applied to an example position on the example patient 130 based on one or more corrected patient size characteristic(s) calculated by the example patient size characteristic calculator 124. In some such examples, the current modulation controller 602 can do each of calculating a radiation dose to be applied to the example patient 130 and control a current applied to the example X-ray emitter 106.

In the illustrated example of FIG. 6, the computation manager 122 further includes the communication interface 604. The communication interface 604 can at least one of transfer data to and receive data from the example CT scanner 102. The communication interface 604 can further at least one of transfer data to and receive data from any component of the computation manager 122, which can include the example patient size characteristic calculator 124, the example patient size characteristic corrector module 126, the processor 128, the current modulation controller 602, the result output interface 606, the database 608 which can, in some such examples, include the lookup table 610, and the CT scanner actuator controller 612.

In some such examples, the communication interface 604 can be implemented by any type of interface standards, such as an Ethernet interface, a universal serial bus (USB), and/or a PCI express interface. Further, the interface standard of the communication interface 604 is to at least one of match the interface of the data port 120 or be converted to match the interface standard of the data port 120, set forth above.

Further included in the computation manager 122 is the result output interface 606. The result output interface 606 can, in some such examples, output one or more result(s) of the CT scan completed by the CT scanner 102. In some such examples, the one or more result(s) of the CT scan can include two dimensional scan data for one or more axial slice(s) of the example patient 130. Additionally or alternatively, the one or more result(s) of the CT scan can include three dimensional scan data for two or more axial slices of the example patient 130. Additionally or alternatively, the one or more results(s) of the CT scan can include one or more graph(s) (e.g., line graph, scatter plot, pie chart, bar graph, etc.) of data for one or more axial slice(s) of the example patient 130. Additionally or alternatively, the one or more result(s) of the CT scan can include any data output readable by at least one of a user and a computer architecture.

The result output interface 606 can be implemented, for example, by display devices (e.g., a light emitting diode (LED), an organic light emitting diode (OLED), a liquid crystal display (LCD), a cathode ray tube display (CRT), a touchscreen, a tactile output device, a printer and/or speakers, etc.

In the illustrated example of FIG. 6, the computation manager 122 includes the database 608 to record data (e.g., scan data, patient size data, correction factor data, etc.). In some examples, the database 608 can store scan data as distributed by the CT scanner 102. Additionally or alternatively, the database 608 can store one or more patient size characteristic(s) as distributed by the example patient size characteristic calculator 124. Additionally or alternatively, the database 608 can store one or more correction factor(s) as distributed by the example patient size characteristic corrector module 126.

The example database 608 can be implemented by a volatile memory (e.g., a Synchronous Dynamic Random Access Memory (SDRAM), a Dynamic Random Access Memory (DRAM), RAMBUS Dynamic Random Access Memory (RDAM), etc.) and/or a non-volatile memory (e.g., flash memory). The example database 608 can additionally or alternatively be implemented by one or more mass storage devices such as hard disk drive(s), compact disk drive(s), digital versatile disk drive(s), solid-state drives(s), etc. While in the illustrated example 608 is illustrated as a single database, the database 608 can be implemented by any number and/or type(s) of databases.

In the illustrated example of FIG. 6, the database 608 further includes the lookup table 610. The example lookup table 610 can, in some such examples, store at least one of one or more patient size characteristic(s), one or more correction factor(s), and one or more corrected patient size characteristic(s) with respect to an axial position and rotational orientation for which the at least one of one or more patient size characteristic(s), one or more correction factor(s), and one or more corrected patient size characteristic(s) were calculated. In some such examples, the lookup table 610 can be implemented by a volatile memory (e.g., a Synchronous Dynamic Random Access Memory (SDRAM), a Dynamic Random Access Memory (DRAM), RAMBUS Dynamic Random Access Memory (RDAM), etc.) to aide in rapid recovery of one or more data point(s). While in the illustrated example the lookup table 610 is illustrated as a single lookup table, the lookup table 610 can be implemented by any number and/or type(s) of lookup tables.

In the illustrated example of FIG. 6, the computation manager 122 further includes a CT scanner actuator controller 612. Generally, the CT scanner actuator controller 612 controls one or more actuator(s) of the CT scanner 102 which, in some such examples, can include the rotational actuator 110, the axial actuator 114, and the vertical actuator 116. In some such examples, the CT scanner actuator controller 612 can command a movement to the rotational actuator 110. Additionally or alternatively, the CT scanner actuator controller 612 can command a movement to the axial actuator 114. Additionally or alternatively, the CT scanner actuator controller 612 can command a movement to the vertical actuator 116. Additionally or alternatively, the CT scanner actuator controller 612 can command a movement to any combination and/or permutation of the actuators set forth above.

In some such examples, the CT scanner actuator controller 612 can additionally determine the current position of one or more actuator(s) which can, in some such examples include the rotational actuator 110, the axial actuator 114 and the vertical actuator 116 of the CT scanner 102. Determining the current position of one or more actuator(s), and thereby a current patient bed axial position and a current X-ray tube rotational orientation, can be implemented into the CT scanner actuator controller 612, for example, by an encoder, a potentiometer, and/or other hardware or software device capable of determining a position of an actuator, for example.

In some such examples, during operation, the CT scanner 102 and computation manager 122 function together to perform a complete CT scan on the example patient. Operation of the CT scanner 102 and computation manager 122 begins with, in response to a command at the input panel 118, the vertical actuator 116 of the example patient bed 112 translating an example patient 130 to an approximate isocenter of an opening of the X-ray tube 104. Further, rotational actuator 110 of the X-ray tube 104 and the example axial actuator 114 of the example patient bed 112 move the example patient 130, the example X-ray emitter 106, and the one or more X-ray detector(s) 108 into the proper position to obtain a first CT scan localizer image with the X-ray emitter 106 and the one or more X-ray detector(s) 108. Upon completion of the first CT scan localizer image, in some such examples taken in a lateral orientation (as used herein, further defined as a "lateral CT localizer image" or "lateral localizer orientation"), the rotational actuator 110 of the X-ray tube 104 rotates the X-ray emitter 106 and the one or more X-ray detector(s) 108 into a position to acquire a second CT scan localizer image, captured in at least one of an anteroposterior or posteroanterior orientation. Further, the data port 120 transmits at least one of the first and second CT scan localizer image(s) to the example communication interface 604 of the example computation manager 122. The communication interface 604 further distributes at least one of the first and second CT scan localizer image(s) to at least one of the example patient size characteristic calculator 124 and the example patient size characteristic corrector module 126. Further, the example patient size characteristic calculator 124 calculates one or more patient size characteristic(s) for one or more axial slice(s) along a height of the example patient 130 and the example patient size characteristic corrector module 126 calculates one or more correction factor(s) for a subset of the one or more patient size characteristic(s) calculated by the example patient size characteristic calculator 124. The example patient size characteristic calculator 124 then applies the one or more correction factor(s) to the subset of the one or more patient size characteristic(s) (e.g., the one or more patient size characteristic(s) is(are) multiplied by the one or more correction factor(s)). Further, the example patient size calculator 124 distributes the one or more corrected patient size characteristic(s) to the lookup table 610, contained in the database 608. Using the one or more corrected patient size characteristic(s) stored in the lookup table 610, the processor 128, the current modulation controller 602, and the CT scanner actuator controller 612 control the CT scanner 102 to complete a full CT scan on the example patient 130. Further, results/scan data of the full CT scan can be distributed to at least one of the result output interface 606 and the database 608.

Thus, when the size of the patient 130 is initially underestimated, for example, the computation manager 122 calculates the corrected patient size characteristic(s) and controls the CT scanner 102 such that the imaging quality of the scans is not reduced (e.g., a smaller than necessary dose, in some examples, is applied when the size of the patient 130 is underestimated and a correction factor is not utilized). In other examples, when the size of the patient 130 is initially overestimated, for example, the computation manager 122 calculates the corrected patient size characteristic(s) and controls the CT scanner 102 such that a proper dose of radiation is applied to the patient 130 (e.g., a larger than necessary dose, in some examples, is applied when the size of the patient 130 is overestimated and a correction factor is not utilized).

Figure 7:
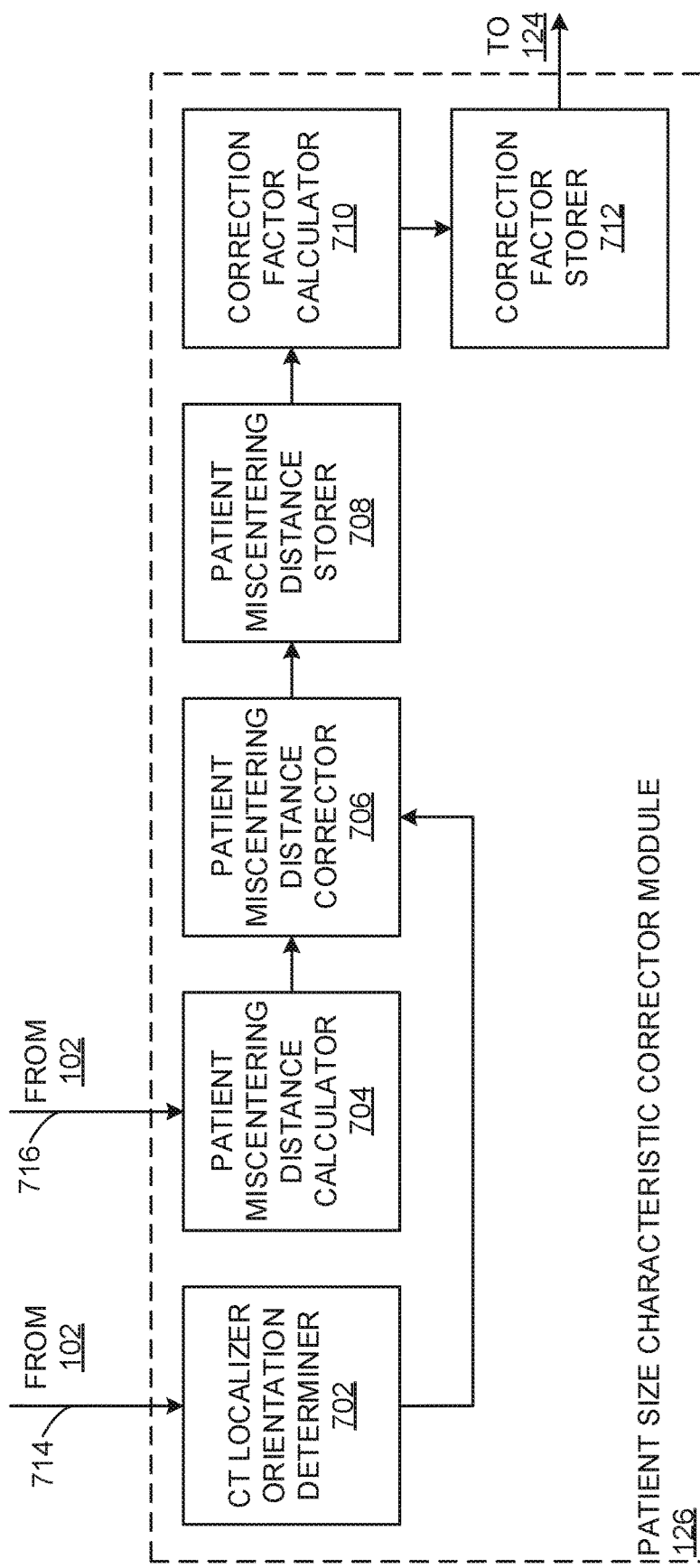
FIG. 7 is a block diagram of an example patient size characteristic corrector module of the example computation manager of FIG. 6.

A block diagram further detailing the example patient size characteristic corrector module 126 of FIG. 6 is illustrated in FIG. 7. The example patient size characteristic corrector module 126 can correct one or more erroneous patient size characteristic(s) calculated by the example patient size characteristic calculator 124, wherein an error in the one or more patient size characteristic(s) is due to the example patient bed 112 not being positioned at the isocenter of the X-ray tube 104 by the vertical actuator 116.

Turning to FIG. 7, the example patient size characteristic corrector module 126 further includes a CT localizer orientation determiner 702, a patient miscentering distance calculator 704, a patient miscentering distance corrector 706, a patient miscentering distance storer 708, a correction factor calculator 710, a correction factor storer 712, and example data feed(s) 714, and 716.

In the illustrated example of FIG. 7, the example patient size characteristic corrector module 126 further includes the CT localizer orientation determiner 702. The CT localizer orientation determiner 702 receives the data feed 714 from the CT scanner 102 which further includes a second CT scan localizer image. In response to receiving data feed 714 from the CT scanner 102, the CT localizer orientation determiner 702 determines the orientation at which the second CT scan localizer image was taken (e.g., anteroposterior orientation or posteroanterior orientation). The CT localizer orientation determiner 702 further distributes the second CT scan localizer image orientation to the example patient miscentering distance corrector 706.

In some such examples, the CT localizer orientation determiner 702 can distribute a message denoting the second CT scan localizer image is in the anteroposterior orientation to the example patient miscentering distance corrector 706. Additionally or alternatively, the CT localizer orientation determiner 702 can distribute a message denoting the second CT scan localizer image is in the posteroanterior orientation to the example patient miscentering distance corrector 706. Additionally or alternatively, the CT localizer orientation determiner 702 can distribute a message denoting the second CT scan localizer image as unavailable. In such examples, correction of one or more patient size characteristic(s) may not be possible.

In the illustrated example of FIG. 7, the example patient size characteristic corrector module 126 further includes the example patient miscentering distance calculator 704. The example patient miscentering distance calculator 704 receives data feed 716 from the CT scanner 102, wherein the data feed 716 includes the first CT scan localizer image taken in the lateral orientation. In response to receiving the first CT scan localizer image (as illustrated with the surrounding CT scanner 102 in FIG. 5), the example patient miscentering distance calculator 704 calculates one or more patient miscentering distance(s) 520 for one or more axial slice(s), examples of which include example axial slice(s) 514, 516, and/or 518, along a height of the example patient 502.

The example patient miscentering distance 520 can further be defined by the distance between the example CT scanner centerline 510 and the example patient centerline 512. Additionally, the one or more axial slice(s), examples of which include example axial slice(s) 514, 516, and/or 518 can include a set of axial slice(s) adjacent to one another over a pre-defined area of interest (e.g., a certain organ or region to be scanned, an entirety of example patient, etc.) along a height of the example patient 502. The unit applied to the example patient miscentering distance 520 can further be any unit by which distance is measured (e.g., inches, millimeters, feet, pixels, any form of arbitrary distance measurement, etc.).

In some such examples, for the example axial slice 514, an example distance between the example X-ray emitter 506 and the example CT scanner centerline 510 is smaller than an example distance between the example X-ray emitter 506 and the example patient centerline 512. Therefore, at axial slice 514, the example patient miscentering distance calculator 704 determines the example patient miscentering distance 520 to be a positive value.

Additionally or alternatively, for the example axial slice 516, an example distance between the example X-ray emitter 506 and the example CT scanner centerline 510 is larger than an example distance between the example X-ray emitter 506 and the example patient centerline 512. Therefore, at axial slice 516, the example patient miscentering distance calculator 704 determines the example patient miscentering distance 520 to be a negative value.

Additionally or alternatively, for the example axial slice 518, an example distance between the example X-ray emitter 506 and the example CT scanner centerline 510 is equal to an example distance between the example X-ray emitter 506 and the example patient centerline 512. Therefore, at axial slice 518, the example patient miscentering distance calculator 704 determines the example patient miscentering distance 520 to be a zero (0) value.

In the illustrated example of FIG. 7, the example patient size characteristic corrector module 126 further includes the example patient miscentering distance corrector 706. In response to receiving a second CT scan localizer image orientation from the CT localizer orientation determiner 702, the example patient miscentering distance corrector 706 corrects one or more patient miscentering distance(s), as calculated by the example patient miscentering distance calculator 704.

In some such examples, in response to receiving a message that the second CT scan localizer image is in the posteroanterior orientation, the example patient miscentering distance corrector 706 maintains one or more patient miscentering distance(s), as calculated by the example patient miscentering distance calculator 704.

Additionally or alternatively, in response to receiving a message that the second CT scan localizer image is in the anteroposterior orientation, the example patient miscentering distance corrector 706 reverses the sign (e.g., multiply by −1, etc.) for one or more patient miscentering distance(s), as calculated by the miscentering distance calculator 704.

In the illustrated example of FIG. 7, the example patient size characteristic corrector module 126 further includes the example patient miscentering distance storer 708. In response to receiving one or more patient miscentering distance(s) from the example patient miscentering distance corrector 706, the example patient miscentering distance storer 708 stores a subset of the example patient miscentering distance(s).

The example patient miscentering distance storer 708 can be implemented by a volatile memory (e.g., a Synchronous Dynamic Random Access Memory (SDRAM), a Dynamic Random Access Memory (DRAM), RAMBUS Dynamic Random Access Memory (RDRAM), etc.) and/or a non-volatile memory (e.g., flash memory). The example patient miscentering distance storer 708 can additionally or alternatively be implemented by one or more mass storage devices such as hard disk drive(s), compact disk drive(s), digital versatile disk drive(s), solid-state drives(s), etc. While the illustrated example patient miscentering distance storer 708 is illustrated as a database, the example patient miscentering distance storer 708 can be implemented by any number and/or type(s) of databases.

In the illustrated example of FIG. 7, the example patient size characteristic corrector module 126 further includes the correction factor calculator 710. In response to receiving one or more patient miscentering distance(s) as stored by the example patient miscentering distance storer 708, the correction factor calculator 710 calculates a set of correction factor(s) (CF(s)) based on a subset of patient miscentering distance(s).

In some such examples, calculating one or more correction factor(s) utilizes the property of similar triangles stating that two or more corresponding sides of two or more similar triangles are proportional. In the example of the correction factor calculator 710, the two or more similar triangles considered are, from FIG. 3, at least one of ΔAKI and ΔAJC, or ΔAKH and ΔAJB.

Using the aforementioned property of similar triangles, it can be stated that the ratio of line AK to line AJ are proportional to each of line KI to line JC and line KH to line JB. Therefore, the correction factor (CF) can be, in some such examples, calculated using the line lengths set forth above, as in Equation (6) shown below:

$$CF = 2\frac{AK}{AJ} \qquad \text{Equation (6)}$$

Further, turning to FIG. 5, the above teachings can be related to the example patient miscentering distance 520 previously presented. In such examples, line AK can be further defined as the example patient miscentering distance 520 (ΔY) subtracted from line A0, which can be further defined as a distance from the example X-ray emitter 506 to the CT scanner centerline 510. Additionally, line AJ can further be defined as the distance from the example X-ray emitter 506 to the X-ray detector 508. Therefore, the correction factor can be, in some such examples, calculated using the line lengths set forth above as in Equation (7) shown below:

$$CF = 2\frac{A0 - \Delta Y}{AJ} \qquad \text{Equation (7)}$$

In some such examples, a nomenclature of line AO can additionally or alternatively read as the source to isocenter distance SI, and a nomenclature of line AJ can additionally or alternatively read as the source to detector distance SD. Therefore, the correction factor can be, using the nomenclature described above, further defined as in Equation (8) shown below:

$$CF = 2\frac{SI - \Delta Y}{SD} \qquad \text{Equation (8)}$$

Further, in each of the examples set forth above, variables A0, AJ, SI, and SD are each constant for an example CT scanner 102.

Upon completion of the calculation of one or more correction factor(s) for one or more axial slice(s) of an example patient by the correction factor calculator 710, the one or more correction factor(s) can be, in some such examples, distributed to the correction factor storer 712. Additionally or alternatively, the one or more correction factor(s) for one or more axial slice(s) of an example patient can instead by applied directly to one or more patient size characteristic(s) (e.g., the one or more patient size characteristic(s) is(are) multiplied by the one or more correction factor(s)) as calculated by the example patient size characteristic calculator 124. Additionally or alternatively, in response to one or more correction factors as calculated by the correction factor calculator 710 equaling a value outside of a pre-defined range, determining that the one or more correction factors equaling a value outside of a pre-defined range are not to be stored in the correction factor storer 712 or applied directly to one or more size characteristics calculated by the example patient size characteristic calculator 124.

In the illustrated example of FIG. 7, the example patient size characteristic corrector module 126 further includes the correction factor storer 712. In response to receiving one or more correction factor(s) from the correction factor calculator 710, the example correction factor storer 712 stores a subset of the correction factor(s).

The correction factor storer 712 can be implemented by a volatile memory (e.g., a Synchronous Dynamic Random Access Memory (SDRAM), a Dynamic Random Access Memory (DRAM), RAMBUS Dynamic Random Access Memory (RDRAM), etc.) and/or a non-volatile memory (e.g., flash memory). The example correction factor storer 712 can additionally or alternatively be implemented by one or more mass storage devices such as hard disk drive(s), compact disk drive(s), digital versatile disk drive(s), solid-state drives(s), etc. While in the illustrated example correction factor storer 712 is illustrated as a database, the correction factor storer 712 can be implemented by any number and/or type(s) of databases.

During operation, the example patient size characteristic corrector module 126 receives a second CT scan localizer image via data feed 714 at the CT localizer orientation determiner 702 and a first CT scan localizer image via data feed 716 at the example patient miscentering distance calculator 704. The CT localizer orientation determiner 702 determines whether the second CT scan localizer image from data feed 714 is in the anteroposterior or posteroanterior orientation and distributes the result to the example patient miscentering distance corrector 706. The example patient miscentering distance calculator 704 determines one or more patient miscentering distance(s) based upon the first CT scan localizer image in the lateral orientation. The one or more patient miscentering distance(s) is(are) further distributed to the example patient miscentering distance corrector 706. In response to receiving one or more patient miscentering distance(s) and the orientation of the second CT scan localizer image, the example patient miscentering distance corrector 706 corrects the one or more patient miscentering distance(s). Now corrected, the one or more patient miscentering distance(s) is(are) stored in the example patient miscentering distance storer 708, and is(are) further distributed to the correction factor calculator 710. The correction factor calculator 710 calculates one or more correction factor(s) for one or more patient size characteristic(s) for one or more axial slice(s) of the example patient 130. The one or more correction factor(s) is(are) further at least one of stored in a correction factor storer 712 and applied directly to one or more patient size characteristic(s) as calculated by the example patient size characteristic calculator 124.

Figure 8:
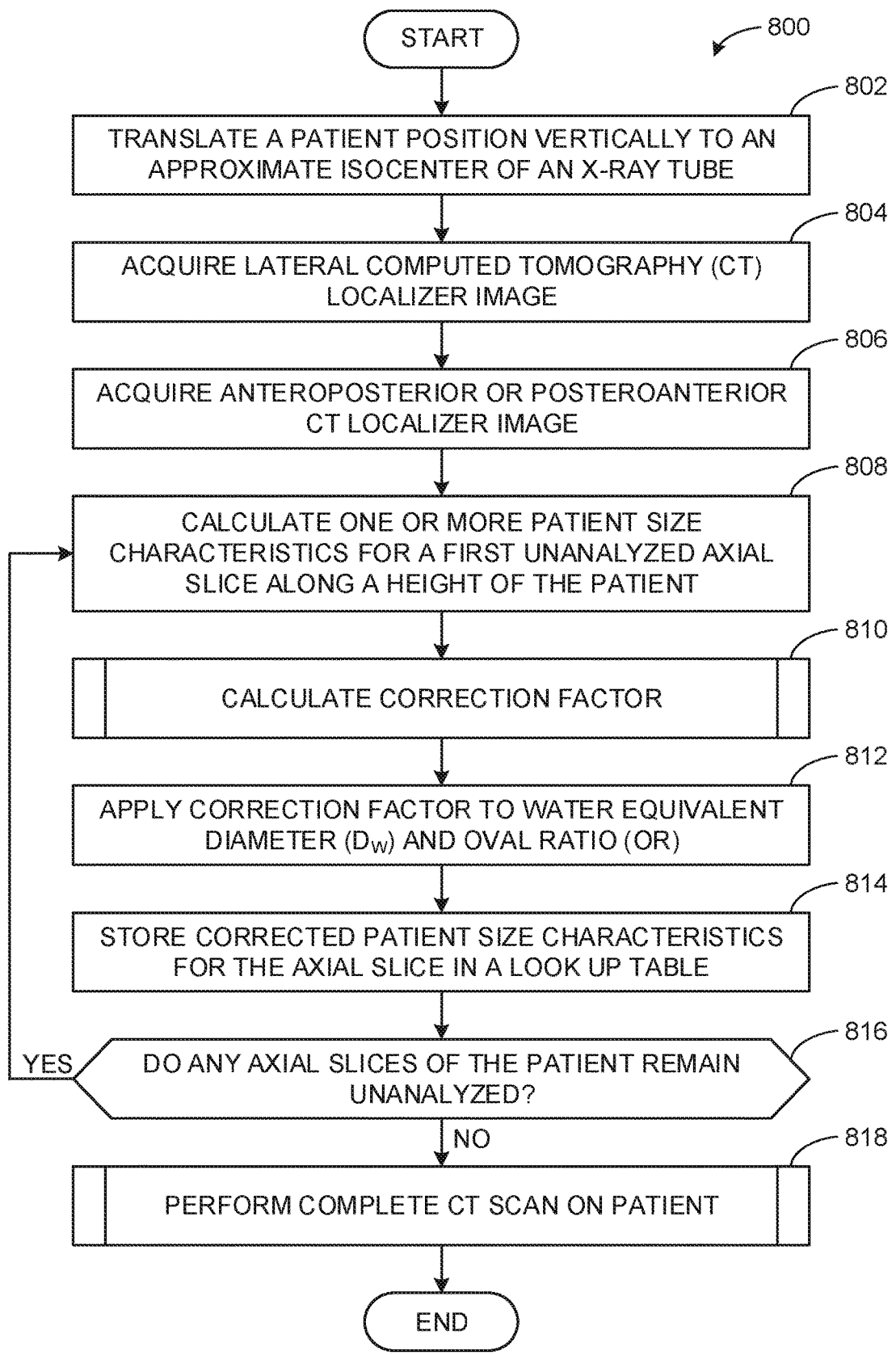
FIG. 8 is a flowchart representative of example machine-readable instructions that can be executed to implement the example CT scanner and computation manager of FIG. 6.
Figure 9:
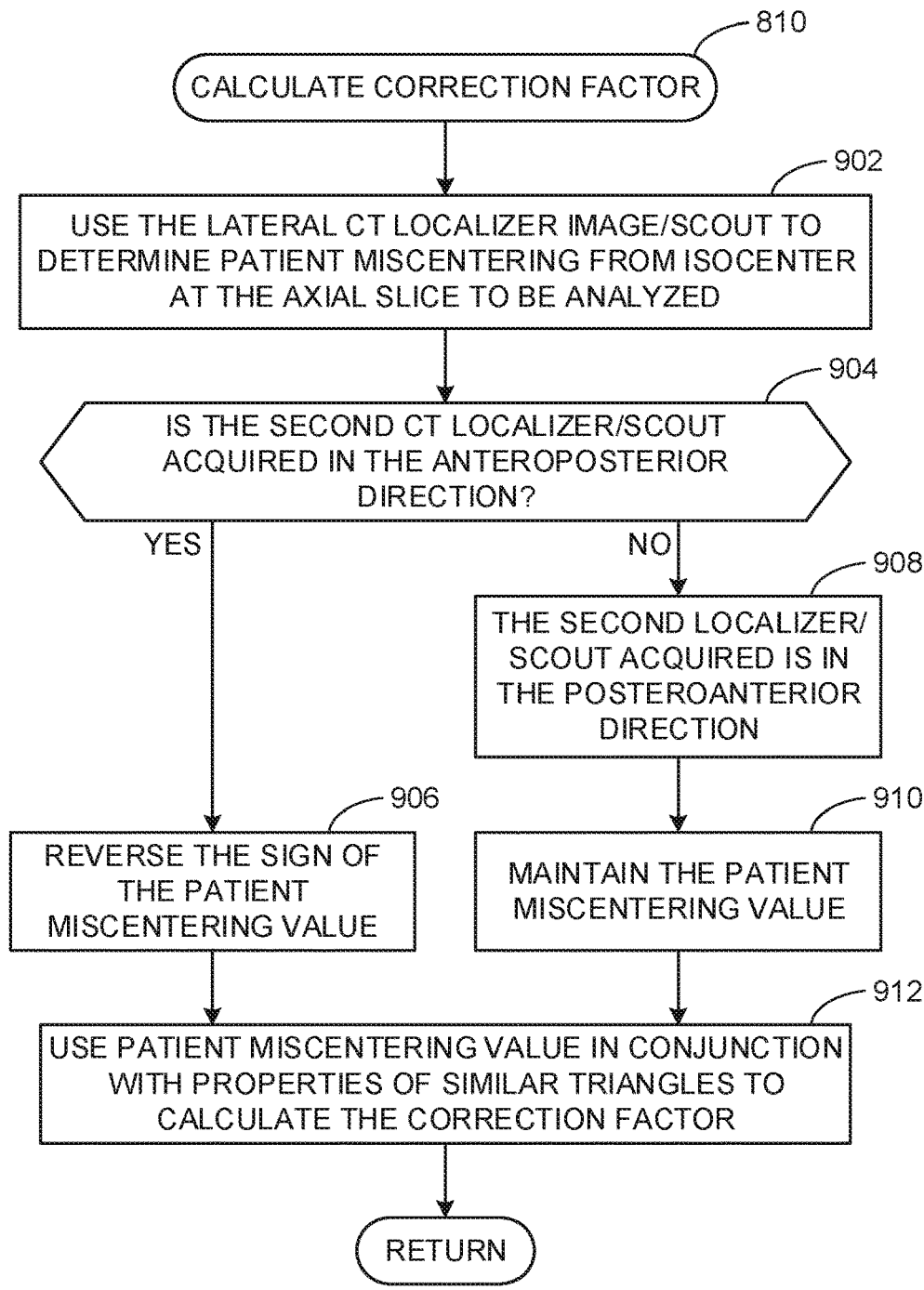
FIG. 9 is a flowchart representative of example machine-readable instructions that can be executed to implement the example patient size characteristic corrector module of FIG. 7.
Figure 10:
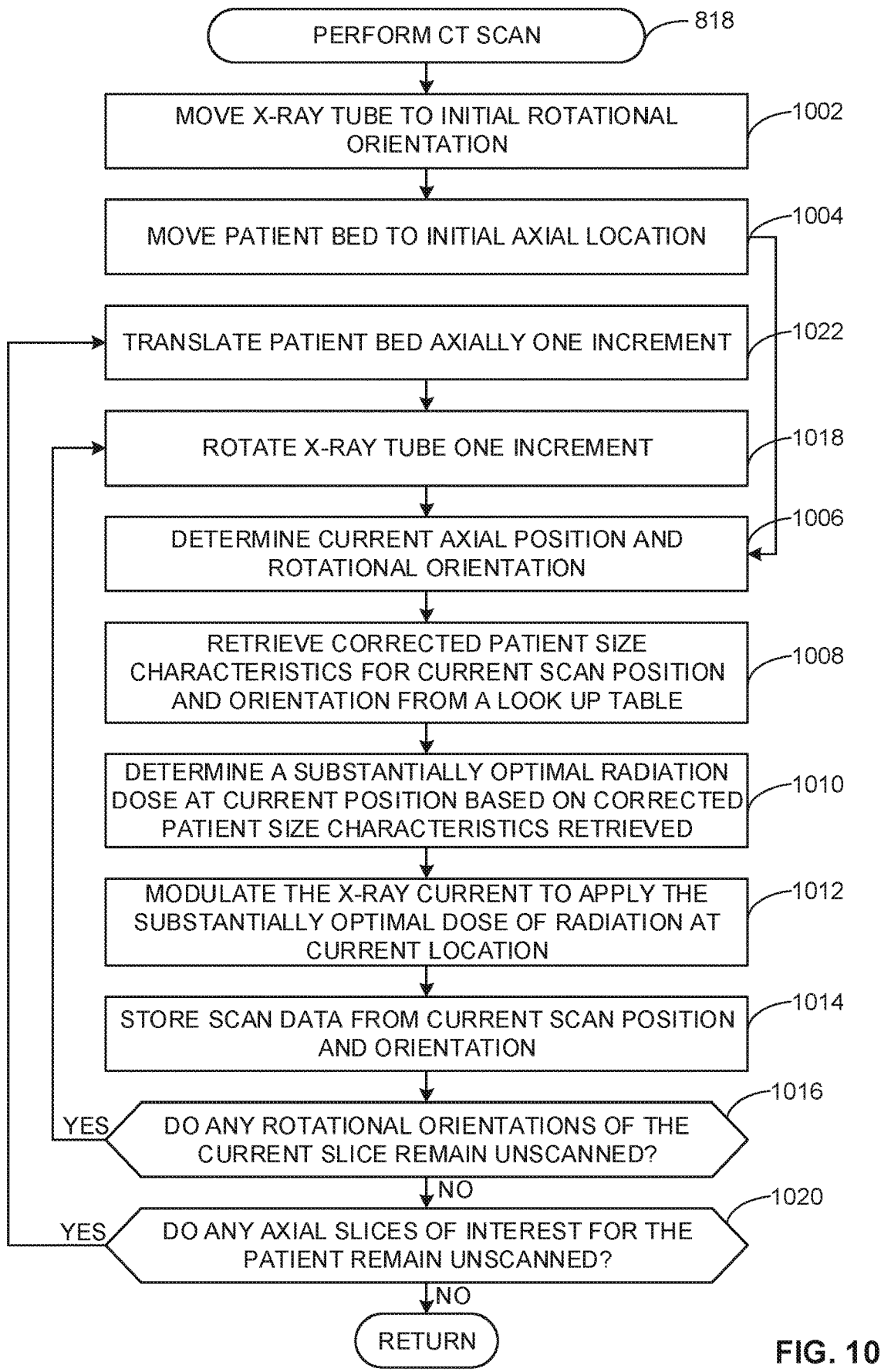
FIG. 10 is a flowchart representative of example machine-readable instructions that can be executed to further implement the example CT scanner and computation manager of FIG. 6.

While an example manner of implementing the example system 100 of FIG. 6 is illustrated in FIGS. 8-10, one or more of the elements, processes and/or devices illustrated in FIGS. 6-7 can be combined, divided, re-arranged, omitted, eliminated and/or implemented in any other way. Further, the example CT scanner 102 which can, in some examples, contain the example X-ray tube 104 which can, in some examples contain the example X-ray emitter 106, the example one or more X-ray detector(s) 108, and the example rotational actuator 110, the example patient bed 112 which can, in some examples, contain the example axial actuator 114, and example vertical actuator 116, the example input panel 118, and the example data port 120, and the example computation manager 122 which can, in some examples, contain the example patient size characteristic calculator 124, the example patient size characteristic corrector module 126 which can, in some examples, contain the example CT localizer orientation determiner 702, the example patient miscentering distance calculator 704, the example patient miscentering distance corrector 706, the example patient miscentering distance storer 708, the example correction factor calculator 710, and the example correction factor storer 712, the example processor 128, the example current modulation controller 602, the example communication interface 604, the example result output interface 606, the example database 608 which can, in some examples, contain the lookup table 610, and the example CT scanner actuator controller 612 and/or, more generally, the example system 100 of FIG. 6 can be implemented by hardware, software, firmware and/or any combination of hardware, software and/or firmware. Thus, for example, any of the example CT scanner 102 which can, in some examples, contain the example X-ray tube 104 which can, in some examples contain the example X-ray emitter 106, the example one or more X-ray detector(s) 108, and the example rotational actuator 110, the example patient bed 112 which can, in some examples, contain the example axial actuator 114, and example vertical actuator 116, the example input panel 118, and the example data port 120, and the example computation manager 122 which can, in some examples, contain the example patient size characteristic calculator 124, the example patient size characteristic corrector module 126 which can, in some examples, contain the example CT localizer orientation determiner 702, the example patient miscentering distance calculator 704, the example patient miscentering distance corrector 706, the example patient miscentering distance storer 708, the example correction factor calculator 710, and the example correction factor storer 712, the example processor 128, the example current modulation controller 602, the example communication interface 604, the example result output interface 606, the example database 608 which can, in some examples, contain the lookup table 610, and the example CT scanner actuator controller 612 and/or, more generally, the example system 100 can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example CT scanner 102 which can, in some examples, contain the example X-ray tube 104 which can, in some examples contain the example X-ray emitter 106, the example one or more X-ray detector(s) 108, and the example rotational actuator 110, the example patient bed 112 which can, in some examples, contain the example axial actuator 114, and example vertical actuator 116, the example input panel 118, and the example data port 120, and the example computation manager 122 which can, in some examples, include the example patient size characteristic calculator 124, the example patient size characteristic corrector module 126 which can, in some examples, include the example CT localizer orientation determiner 702, the example patient miscentering distance calculator 704, the example patient miscentering distance corrector 706, the example patient miscentering distance storer 708, the example correction factor calculator 710, and the example correction factor storer 712, the example processor 128, the example current modulation controller 602, the example communication interface 604, the example result output interface 606, the example database 608 which can, in some examples, include the lookup table 610, and the example CT scanner actuator controller 612 is/are hereby expressly defined to include a non-transitory computer readable storage device or storage disk such as a memory, a digital versatile disk (DVD), a compact disk (CD), a Blu-ray disk, etc. including the software and/or firmware. Further still, the example system 100 of FIG. 6 can include one or more elements, processes and/or devices in addition to, or instead of, those illustrated in FIG. 1, and/or can include more than one of any or all of the illustrated elements, processes and devices.

A flowchart representative of example machine-readable instructions for implementing the example system 100 of FIG. 6 is shown in FIGS. 8-10. In this example, the machine-readable instructions comprise a program for execution by a processor such as the processor 1112 shown in the example processor platform 1100 discussed below in connection with FIGS. 8-10. The program can be embodied in software stored on a non-transitory computer readable storage medium such as a CD-ROM, a floppy disk, a hard drive, a digital versatile disk (DVD), a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowcharts illustrated in FIGS. 8-10, many other methods of implementing the example system 100 can alternatively be used. For example, the order of execution of the blocks can be changed, and/or some of the blocks described can be changed, eliminated, or combined. Additionally or alternatively, any or all of the blocks can be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIGS. 8-10 can be implemented using coded instructions (e.g., computer and/or machine-readable instructions) stored on a non-transitory computer and/or machine-readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. can be present without falling outside the scope of the corresponding claim. As used herein, when the phrase "at least" is used as the transition term in a preamble of a claim, it is open-ended in the same manner as the term "comprising" and "including" are open ended.

FIG. 8 is a flowchart representative of an example machine-readable instructions that can be performed by the example system 100 of FIG. 6. The program of FIG. 8 begins at block 802, at which the example CT scanner 102, further including the example patient bed 112 which further includes the vertical actuator 116, attempts to translate or move the example patient 130 to an isocenter of the X-ray tube 104.

At block 804, in response to identifying that the example patient 130 is located at the isocenter of the X-ray tube 104 within a stated tolerance (e.g., a tolerance of +/−2.0 centimeters, etc.), the X-ray emitter 106 and the one or more X-ray detector(s) 108 are utilized to acquire the first CT scan localizer image in the lateral orientation.

At block 806, in response to completing the first CT scan localizer image in the lateral orientation, the rotational actuator 110 rotates the X-ray emitter 106 and the one or more X-ray detector(s) 108 into an orientation to acquire a second CT scan localizer image, in at least one of an anteroposterior or posteroanterior orientation.

At block 808, using the second CT scan localizer image in at least one of an anteroposterior or posteroanterior orientation acquired at block 806 by the X-ray emitter 106 and one or more X-ray detector(s) 108, the patient size characteristic calculator 124 calculates one or more patient size characteristic(s) for a first unanalyzed axial slice along a height of the example patient 130. In some such examples, the one or more patient size characteristic(s) calculated can include water equivalent diameter, patient width, patient thickness, projection area, projection measure, and/or oval ratio, etc.

At block 810, in response to receiving one or more patient size characteristic(s) calculated at block 808 for the first unanalyzed axial slice along the height of the example patient 130, the example patient size characteristic corrector module 126 calculates one or more correction factor(s) for one or more patient size characteristic(s) based on a patient miscentering distance calculated by the example patient miscentering distance calculator 704 based upon the first CT scan localizer image in the lateral orientation.

At block 812, in response to receiving one or more correction factor(s) for one or more patient size characteristic(s) calculated at block 810, the example patient size characteristic calculator 124 applies one or more correction factor(s) to one or more patient size characteristic(s) (e.g., the one or more patient size characteristic(s) is(are) multiplied by the one or more correction factor(s)). In some such examples, one or more patient size characteristic(s) can include water equivalent diameter, patient width, patient thickness, projection area, projection measure, and/or oval ratio, etc.

At block 814, in response to identifying one or more corrected patient size characteristic(s) as calculated by the example patient size characteristic calculator 124, the database 608 stores the one or more corrected patient size characteristic(s) in a lookup table 610. Further, the corrected patient size characteristic(s) stored in the lookup table 610 are stored relative to an axial slice and a rotational orientation for which the one or more corrected patient size characteristic(s) were calculated.

At block 816, in response to the one or more corrected patient size characteristic(s) from the first unanalyzed axial slice along the height of the example patient being stored in the lookup table 610, the CT scanner actuator controller 612 determines whether any axial slices of interest of the example patient 130 remain unanalyzed. In response to determining that one or more additional axial slices of the example patient 130 remain unanalyzed, processing returns to block 808. Alternatively, in response to determining that each axial slice of interest of the example patient 130 has been analyzed, processing transfers to block 818.

At block 818, in response to identifying that each axial slice of interest of the example patient 130 has been analyzed, the example system 100, further including the CT scanner 102 and the computation manager 122, performs a full CT scan on the area of interest of the example patient 130.

Additional detail in connection with calculating a correction factor (FIG. 8, block 810) is shown in FIG. 9. FIG. 9 is a flowchart of machine-readable instructions that can be performed by the example patient size characteristic corrector module 126 of FIG. 7. The example method begins at block 902, at which the example patient size characteristic corrector module 126 determines, for the example patient 130, a patient miscentering value from an isocenter of the X-ray tube 104, which further includes obtaining the first CT scan localizer image in the lateral direction from the CT scanner 102 in the data feed 714.

Further at block 902, in response to receiving the first CT scan localizer image from the CT scanner 102 in the data feed 714 (as illustrated with the surrounding CT scanner 102 in FIG. 5), the example patient miscentering distance calculator 704 calculates the example patient miscentering distance for the axial slice along a height of the example patient 130 to be analyzed.

At block 904, in response to receiving a patient miscentering distance calculated at block 902, the CT localizer orientation determiner 702 determines whether the second CT scan localizer image, acquired from the CT scanner 102 in the data feed 716, was acquired in the anteroposterior orientation.

At block 906, in response to the CT localizer orientation determiner 702 identifying the second CT scan localizer image to be in the anteroposterior orientation at block 904, the example patient miscentering distance corrector 706 reverses the sign of the example patient miscentering distance. For example, if the localizer image was acquired in the anteroposterior orientation, then the miscentering value should be subtracted, rather than added, in the correction factor. As a result, the patient miscentering value is reversed or negated (e.g., multiplied by −1, etc.) to adjust the correction factor appropriately.

At block 908, in response to block 904 identifying that the second CT scan localizer image is not in the anteroposterior orientation, the CT localizer orientation determiner 702 determines that the second CT scan localizer image is in the posteroanterior orientation.

At block 910, in response to block 908 identifying that the second CT scan localizer image is in the posteroanterior orientation, the example patient miscentering distance corrector 706 maintains the example patient miscentering distance previously calculated at block 902 (e.g., the value does not have to be inverted or negated to correctly compute the correction factor, etc.).

At block 912, in response to receiving a patient miscentering distance, now corrected, from at least one of block 906 or block 910, the correction factor calculator 710 uses at least one of Equation (6), Equation (7), and Equation (8) to calculate one or more correction factor(s) for one or more patient size characteristic(s) for the axial slice of the example patient to be analyzed. Additionally or alternatively, in some such examples at block 912, the one or more correction factor(s) calculated will further be applied to one or more patient size characteristic(s) (i.e., the one or more patient size characteristic(s) is(are) multiplied by the one or more correction factor(s)) by the example patient size characteristic corrector module 126. In response to at least one of calculating and applying one or more correction factor(s) for one or more patient size characteristic(s) being identified as complete, processing returns to block 812 of the example machine-readable instructions of FIG. 8.

Additional detail in connection with performing a complete CT scan on the example patient 130 (FIG. 8, block 818) is shown in FIG. 10. FIG. 10 is a flowchart representative of an example method that can be performed by the example system 100 of FIG. 6. The example method begins at block 1002, at which the X-ray tube 104 is rotated to an initial orientation by the rotational actuator 110, further controlled by the CT scanner actuator controller 612.

At block 1004, in response to the X-ray tube 104 completing a rotation to an initial orientation, the example patient bed 112 translates the example patient 130 to an initial axial location using the axial actuator 114, further controlled by the CT scanner actuator controller 612. Further, in some such examples, block 1002 and 1004 can be executed in parallel, with the X-ray tube 104 rotating to an initial orientation at the same time as the example patient bed 112 translates to an initial axial location. Upon each of the X-ray tube 104 and patient bed 112 reaching an initial location, processing transfers to block 1006.

At block 1006, the CT scanner actuator controller 612 determines the current axial position of the example patient bed 112, and the current rotational orientation of the X-ray tube 104 upon completion of motion set forth by block 1004.

At block 1008, in response to receiving at least one of a current rotational orientation of the X-ray tube 104 and a current axial position of the example patient bed 112 as determined by the CT scanner actuator controller 612, the current modulation controller 602 retrieves one or more patient size characteristic(s) for the current rotational orientation of the X-ray tube 104 and the current axial position of the example patient bed 112 from the lookup table 610, as stored by the database 608.

At block 1010, based on the one or more patient size characteristic(s) for the current rotational orientation of the X-ray tube 104 and the current axial position of the example patient bed 112 retrieved from the lookup table 610 at block 1008, the current modulation controller 602 further determines a radiation dose to be applied to the example patient 130 at the current orientation of the X-ray tube 104 and the current axial position of the example patient bed 112.

At block 1012, based on the radiation dose to be applied to the example patient 130 at the current orientation of the X-ray tube 104 and the current axial position of the example patient bed 112 calculated by the current modulation controller 602 at block 1010, the current modulation controller 602 is further to calculate and apply an example X-ray current, correlated to the radiation dose previously calculated, to the X-ray emitter 106.

At block 1014, in response to receiving scan data (e.g., an attenuated X-ray signal emitted by the X-ray emitter 106 detected by the one or more X-ray detector(s) 108), one or more characteristic(s) of the attenuated X-ray for the current rotational orientation of the X-ray tube 104 and the current axial position of the example patient bed 112 are stored in the database 608 as scan data.

At block 1016, in response to storage of scan data for the current rotational orientation of the X-ray tube 104 and the current axial position of the example patient bed 112 in the database 608 being identified as complete, the CT scanner actuator controller 612 determines if any rotational orientations of the X-ray tube 104 at the current axial position of the example patient bed 112 remain unscanned. In response to determining that one or more rotational orientation(s) are unscanned, processing transfers to block 1018. Conversely, in response to determining that each rotational orientation at the current axial position of the patient bed 112 is scanned, processing continues to block 1020.

At block 1018, in response to the CT scanner actuator controller 612 determining, at block 1016, that one or more rotational orientation(s) at the current axial position is(are) unscanned, the X-ray tube 104 is rotated one discrete increment by the rotational actuator 110, further controlled by the CT scanner actuator controller 612. Upon completion of the motion, processing transfers to block 1006.

At block 1020, in response to the CT scanner actuator controller 612 determining, at block 1016, that each rotational orientation of the current axial position is scanned, the CT scanner actuator controller 612 determines if any axial positions of interest along a height of the example patient 130 remain unscanned. In response to determining that one or more axial position(s) of interest is(are) unscanned, processing transfers to block 1022. Conversely, in response to determining that each axial position of interest is scanned, processing returns to the end block of the example machine-readable instructions of FIG. 8.

At block 1022, in response to the CT scanner actuator controller 612 determining, at block 1020, that one or more axial position(s) of interest is(are) unscanned, the example patient bed 112 is translated one discrete increment in the axial direction by the axial actuator 114, further controlled by the CT scanner actuator controller 612. Upon completion of the motion, processing transfers to block 1018.

Figure 11:
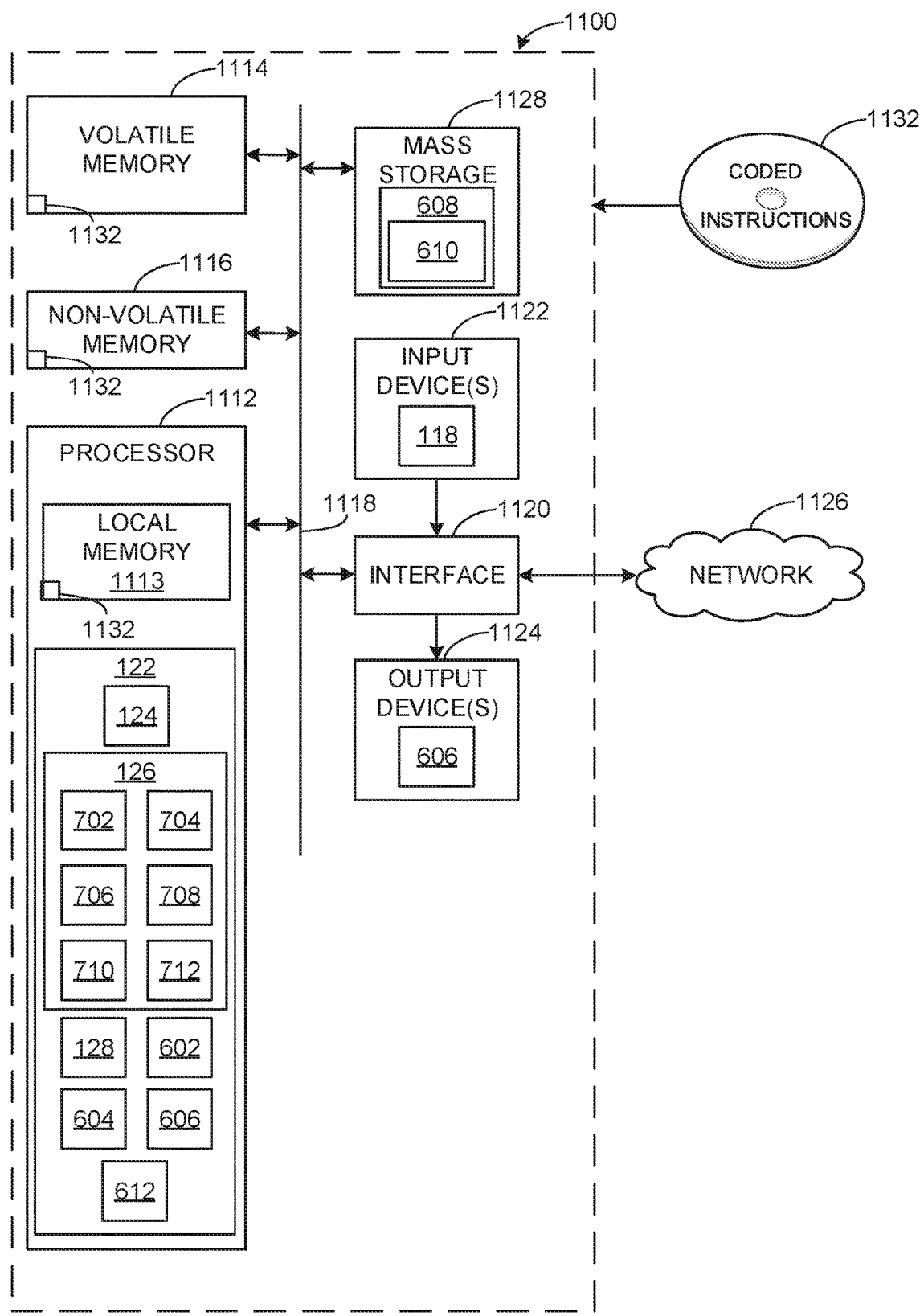
FIG. 11 is a block diagram of an example processing platform structured to execute machine-readable instructions to implement the methods of FIGS. 8-10.

FIG. 11 is a block diagram of an example processor platform 1100 capable of executing the instructions of FIGS. 8-10 to implement the apparatus of FIGS. 6-7. The processor platform 1100 can be, for example, a server, a personal computer, a mobile device (e.g., a cell phone, a smart phone, a tablet such as an iPad™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors or controllers from any desired family or manufacturer. The hardware processor can be a semiconductor based (e.g., silicon based) device. In this example, the processor implements the example computation manager 122 which can, in some examples, contain the example patient size characteristic calculator 124, the example patient size characteristic corrector module 126 which can, in some examples, contain the example CT localizer orientation determiner 702, the example patient miscentering distance calculator 704, the example patient miscentering distance corrector 706, the example patient miscentering distance storer 708, the example correction factor calculator 710, and the example correction factor storer 712, the example processor 128, the example current modulation controller 602, the example communication interface 604, the example result output interface 606, and the example CT scanner actuator controller 612.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 can be implemented by flash memory and/or any other desired type of memory device. Access to the main memory 1114, 1116 is controlled by a memory controller.

The processor platform 1100 of the illustrated example also includes an interface circuit 1120. The interface circuit 1120 can be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 of FIGS. 8-10 can be stored in the mass storage device 1128, in the volatile memory 1114, in the non-volatile memory 1116, and/or on a removable tangible computer readable storage medium such as a CD or DVD.

From the foregoing, it will be appreciated that example methods, apparatus and articles of manufacture have been disclosed that can correct one or more patient size characteristic(s) in Computer Tomography (CT) scanning when a patient is miscentered in the scanning apparatus. The correction of the patient size characteristics can at least 1) help ensure that the quality of the images captured by the scan is retained and 2) help ensure that a larger than necessary dose of radiation is not applied to the patient. Further, the correction factor set forth by the example methods, apparatus and articles of manufacture disclosed can be directly applied to a water equivalent diameter value, long held as a gold standard for calculating patient size in CT scanning.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus to correct a patient size characteristic in Computed Tomography (CT) when a patient is miscentered, the apparatus comprising:
a processor to:
calculate a set of patient size characteristics for a set of axial slices along a height of the patient;
calculate a set of correction factors for the set of patient size characteristics based on a set of patient miscentering distances for the set of axial slices along the height of the patient; and
apply the set of correction factors to the set of patient size characteristics for the set of axial slices along the height of the patient; and
utilize a set of corrected patient size characteristics for the set of axial slices along the height of the patient to perform a CT scan on the patient, when the patient is miscentered, by modulating an X-ray current to control a radiation dose applied to the patient.

2. The apparatus of claim 1, wherein the processor is to select at least one of an anteroposterior localizer orientation, posteroanterior localizer orientation, and lateral localizer orientation for a first and second CT localizer image.

3. The apparatus of claim 2, wherein the processor is to:
calculate, using the lateral CT localizer image, a set of patient miscentering distances for the set of axial slices of the patient; and
in response to an output from the processor including at least one of the anteroposterior and posteroanterior CT localizer orientations, correct the patient miscentering distance.

4. The apparatus of claim 1, wherein the processor is to calculate, utilizing a property of similar triangles stating that two or more corresponding sides of two or more similar triangles are proportional, the set of correction factors.

5. The apparatus of claim 4, wherein calculating the set of correction factors further includes utilizing:

$$CF = 2\frac{SI - \Delta Y}{SD}$$

wherein CF represents correction factor, SI represents source to isocenter distance, $\Delta Y$ represents patient miscentering distance, and SD represents source to detector distance.

6. The apparatus of claim 1, wherein the set of corrected patient size characteristics further include at least one of a water equivalent diameter and oval ratio.

7. The apparatus of claim 1, wherein the processor is to:
determine a current patient bed axial position and X-ray tube rotational orientation;
modulate an X-ray current to apply a radiation dose to the patient at the current patient bed axial position and X-ray tube rotational orientation based upon the set of corrected patient size characteristics; and
store, using a database, a set of scan data from the current patient bed axial position and X-ray tube rotational orientation.

8. A method for correcting patient size characteristics in Computed Tomography (CT) when patients are miscentered, the method comprising:
calculating, using a processor, a set of patient size characteristics, for a set of axial slices along a height of the patient;
calculating, using the processor, a set of correction factors for the set of patient size characteristics based on a set of patient miscentering distances for the set of axial slices along the height of the patient;
applying, using the processor, the set of correction factors to the set of patient size characteristics for the set of axial slices along the height of the patient; and
utilizing, using the processor, a set of corrected patient size characteristics for the set of axial slices along the height of the patient to perform a CT scan on the patient, when the patient is miscentered, by modulating an X-ray current to control a radiation dose applied to the patient.

9. The method of claim 8, wherein calculating the set of corrected patient size characteristics further includes acquiring a first and second CT localizer image in at least one of an anteroposterior localizer orientation, posteroanterior localizer orientation, and lateral localizer orientation.

10. The method of claim 9, wherein calculating a correction factor for the set of patient size characteristics further includes:
determining, using the lateral CT localizer image, a set of patient miscentering distances for the set of axial slices of the patient;
reversing, in response to the second CT localizer image being in the anteroposterior orientation, a sign of the set of patient miscentering distances;
maintaining, in response to the second CT localizer image being in the posteroanterior orientation, the set of patient miscentering distances; and
utilizing the set of patient miscentering distances to calculate the set of correction factors for the set of axial slices of the patient.

11. The method of claim 10, wherein calculating the set of correction factors further includes utilizing:

$$CF = 2\frac{SI - \Delta Y}{SD}$$

wherein CF represents correction factor, SI represents source to isocenter distance, $\Delta Y$ represents patient miscentering distance, and SD represents source to detector distance.

12. The method of claim 8, wherein patient size characteristics can further include at least one of a water equivalent diameter and oval ratio.

13. The method of claim 8, wherein the set of corrected patient size characteristics can be stored in a set of lookup tables.

14. The method of claim 13, wherein utilizing the set of corrected patient size characteristics to perform a complete CT scan on the patient further includes, for a set of rotational orientations of an X-ray tube for a set of axial slices of interest for the patient:
determining a current patient bed axial position and X-ray tube rotational orientation;
retrieving the set of corrected patient size characteristics from the set of lookup tables for the current axial position and rotational orientation of the patient;
modulating an X-ray current to apply a radiation dose to the patient at the current patient bed axial position and the X-ray tube rotational orientation based upon the set of corrected patient size characteristics; and
storing scan data from the current patient bed axial position and X-ray tube rotational orientation.

15. A non-transitory computer readable storage medium comprising machine-readable instructions that, when executed by a processor, cause a machine to at least:
  calculate a set of patient size characteristics, for a set of axial slices along a height of a patient;
  calculate a set of correction factors for the set of patient size characteristics based on a set of patient miscentering distances for the set of axial slices along the height of the patient;
  apply the set of correction factors to the set of patient size characteristics for the set of axial slices along the height of the patient; and
  utilize a set of corrected patient size characteristics for the set of axial slices along the height of the patient to perform a CT scan on the patient, when the patient is miscentered, by modulating an X-ray current to control a radiation dose applied to the patient.

16. The computer readable storage medium of claim 15, wherein the instructions, when executed further cause the machine to acquire a first and second CT localizer image in at least one of an anteroposterior localizer orientation, posteroanterior localizer orientation, and lateral localizer orientation.

17. The computer readable storage medium of claim 16, wherein the machine-readable instructions, when executed, further cause the machine to:
  determine, using the lateral CT localizer image, a set of patient miscentering distances for the set of axial slices of the patient;
  reverse, in response to the second CT localizer image being in the anteroposterior orientation, a sign of the set of patient miscentering distances;
  maintain, in response to the second CT localizer image being in the posteroanterior orientation, the set of patient miscentering distances; and
  utilize the set of patient miscentering distances to calculate the set of correction factors for the set of axial slices of the patient.

18. The computer readable storage medium of claim 17, wherein the instructions, when executed, further cause the machine to calculate one or more correction factors utilizing:

$$CF = 2\frac{SI - \Delta Y}{SD}$$

wherein CF represents correction factor, SI represents source to isocenter distance, $\Delta Y$ represents patient miscentering distance, and SD represents source to detector distance.

19. The computer readable storage medium of claim 15, wherein patient size characteristics can further include at least one of a water equivalent diameter and oval ratio.

20. The computer readable storage medium of claim 15, wherein the set of corrected patient size characteristics can be stored in a set of lookup tables.

21. The computer readable storage medium of claim 20, wherein the instructions, when executed, further cause the machine to, for each rotational orientation of an X-ray tube for each axial slice of interest for the patient:
  determine a current patient bed axial position and X-ray tube rotational orientation;
  retrieve the set of corrected patient size characteristics from the set of lookup tables for the current axial position and rotational orientation of the patient;
  modulate an X-ray current to apply a radiation dose to the patient at the current patient bed axial position and X-ray tube rotational orientation based upon the set of corrected patient size characteristics; and
  store scan data from the current patient bed axial position and X-ray tube rotational orientation.

* * * * *